(12) United States Patent
Lu et al.

(10) Patent No.: US 8,598,138 B2
(45) Date of Patent: Dec. 3, 2013

(54) AMPHIPHILIC NUCLEOTIDE COCHLEATE COMPOSITIONS AND METHODS OF USING THE SAME

(75) Inventors: Ruying Lu, New Providence, NJ (US); Raphael J. Mannino, Glen Gardner, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 0 days.

(21) Appl. No.: 13/370,158

(22) Filed: Feb. 9, 2012

(65) Prior Publication Data

US 2012/0232260 A1 Sep. 13, 2012

Related U.S. Application Data

(63) Continuation of application No. 12/438,266, filed as application No. PCT/US2007/018553 on Aug. 22, 2007, now abandoned.

(60) Provisional application No. 60/839,962, filed on Aug. 23, 2006.

(51) Int. Cl.
| | |
|---|---|
| *A01N 33/12* | (2006.01) |
| *A61K 31/14* | (2006.01) |
| *C07H 21/04* | (2006.01) |
| *C07C 211/00* | (2006.01) |
| *C07C 213/00* | (2006.01) |
| *C07C 215/00* | (2006.01) |
| *C07C 217/00* | (2006.01) |
| *C07C 221/00* | (2006.01) |
| *C07C 223/00* | (2006.01) |
| *C07C 225/00* | (2006.01) |

(52) U.S. Cl.
USPC ......... 514/44 A; 514/642; 536/24.5; 564/281; 564/291

(58) Field of Classification Search
None
See application file for complete search history.

(56) References Cited

U.S. PATENT DOCUMENTS

| | | | | | |
|---|---|---|---|---|---|
| 4,078,052 | A | * | 3/1978 | Papahadjopoulos | 424/450 |
| 4,663,161 | A | * | 5/1987 | Mannino et al. | 424/450 |
| 5,840,707 | A | * | 11/1998 | Mannino et al. | 514/44 A |
| 5,994,318 | A | * | 11/1999 | Gould-Fogerite et al. | 514/44 R |
| 6,153,217 | A | * | 11/2000 | Jin et al. | 424/450 |
| 6,184,372 | B1 | * | 2/2001 | Raveche | 536/24.5 |
| 6,340,591 | B1 | * | 1/2002 | Margolis et al. | 435/320.1 |
| 6,592,894 | B1 | * | 7/2003 | Zarif et al. | 424/450 |
| 6,797,281 | B1 | * | 9/2004 | Pisano et al. | 424/450 |
| 2005/0013854 | A1 | * | 1/2005 | Mannino et al. | 424/450 |
| 2006/0241076 | A1 | * | 10/2006 | Uhlmann et al. | 514/44 |

FOREIGN PATENT DOCUMENTS

| | | |
|---|---|---|
| WO | WO-0037046 A1 | 6/2000 |
| WO | WO 2004/091572 A2 * | 10/2004 |
| WO | WO 2004/091578 A2 * | 10/2004 |
| WO | WO 2005/021722 A2 * | 10/2005 |
| WO | WO-2005110361 A2 | 11/2005 |

* cited by examiner

*Primary Examiner* — Lawrence E Crane
(74) *Attorney, Agent, or Firm* — McCarter & English, LLP; Danielle L. Herritt; Wei Song

(57) ABSTRACT

The present invention is directed to siRNA-cochleate compositions that include a siRNA that is associated with a cochleate and a positively charged amphiphile. The present invention also includes methods for making and using the compositions provided herein.

10 Claims, 9 Drawing Sheets

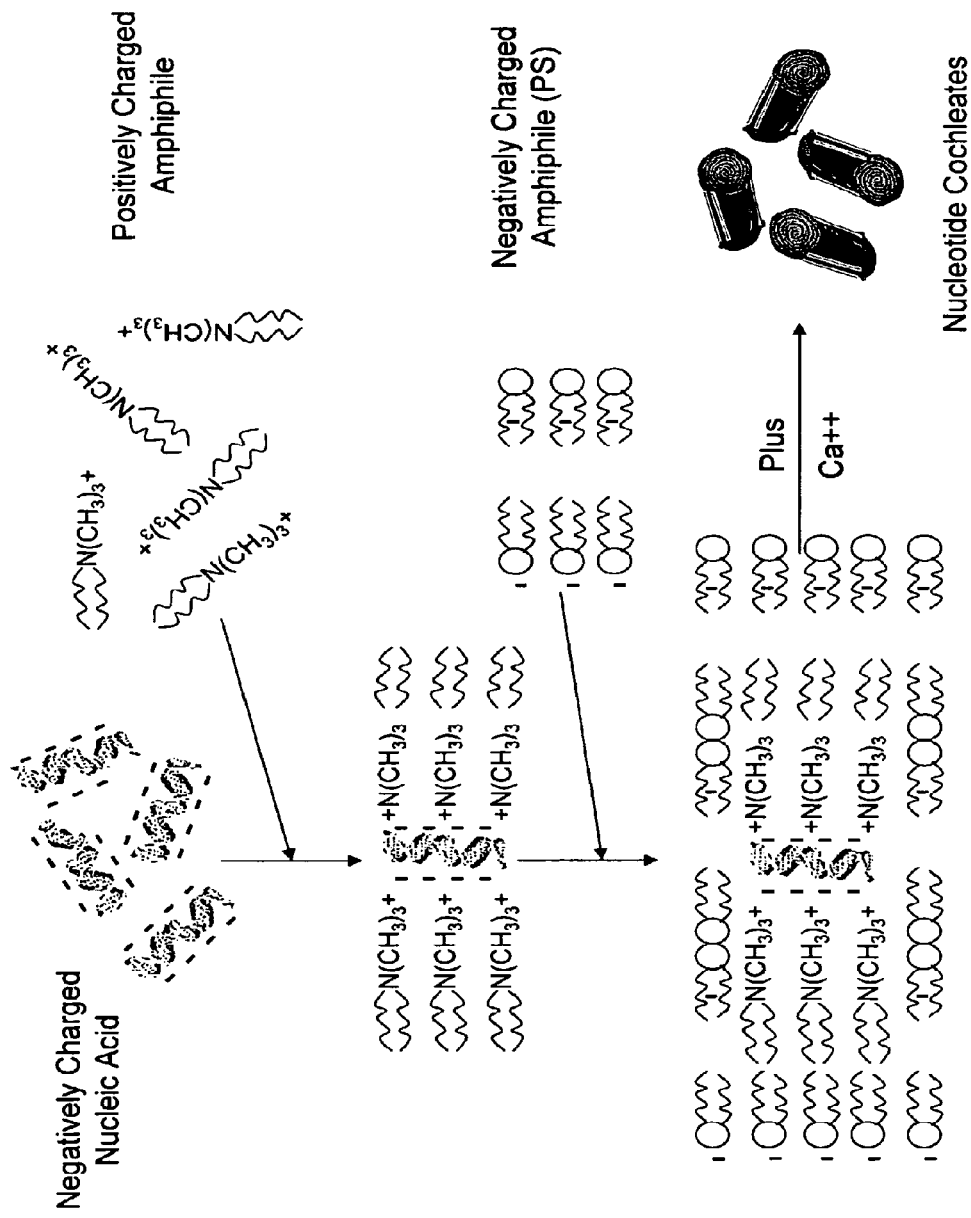

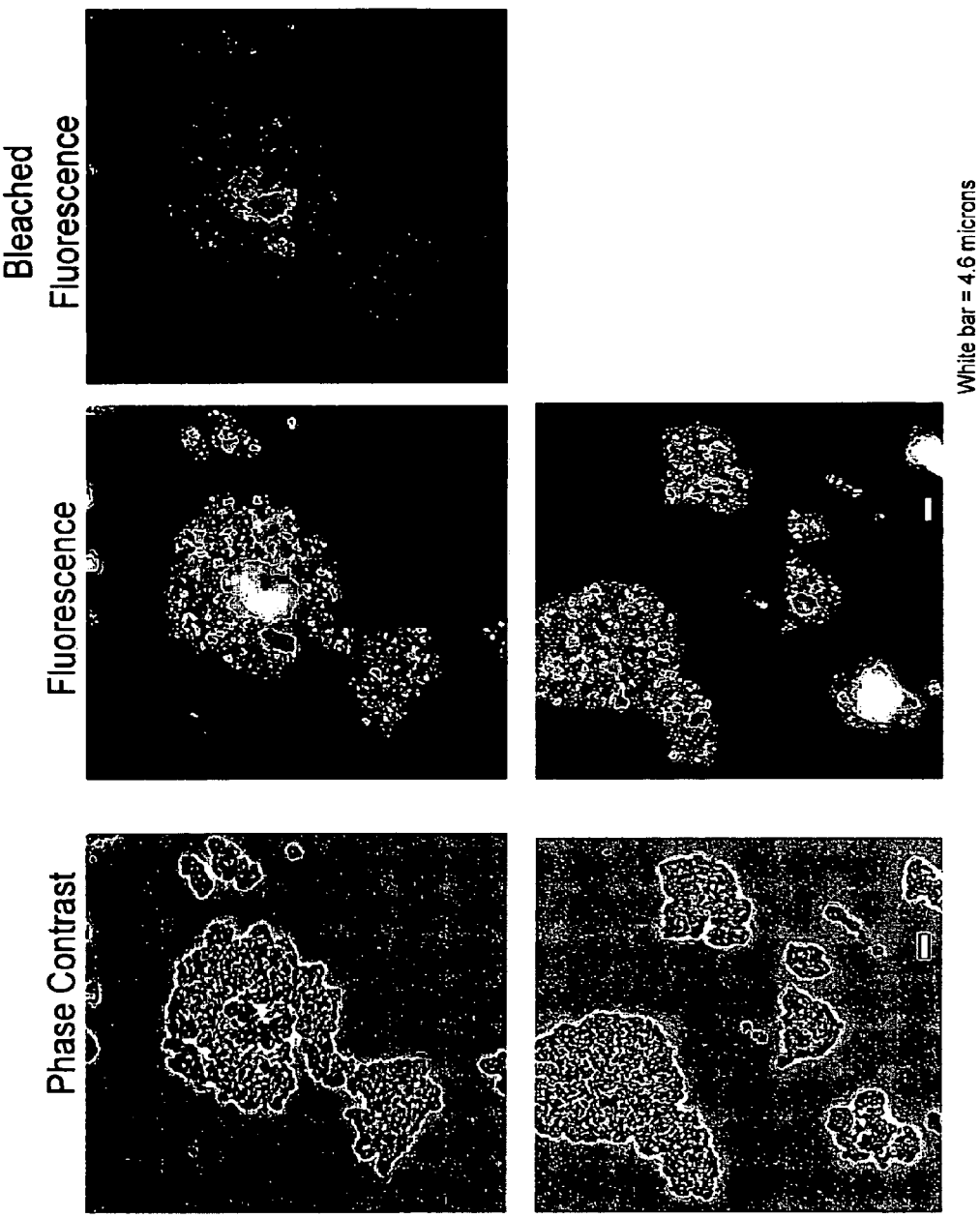

Background stain

NFkB H3 decoy

Formulation #4

Formulation #3

Formulation #1

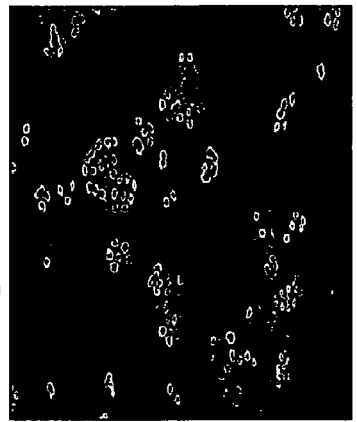
Figure 4A Background stain
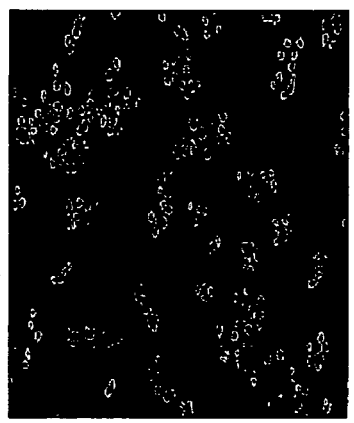
Figure 4B NFkB PS decoy
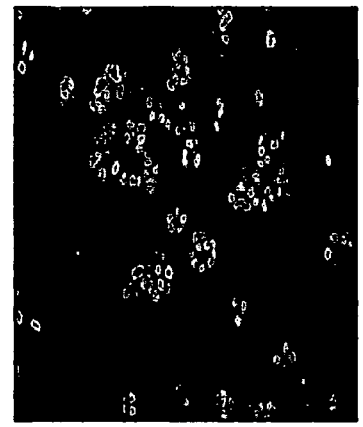
Figure 4E Formulation #7
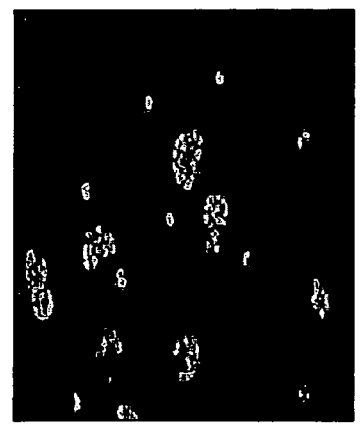
Figure 4D Formulation #6
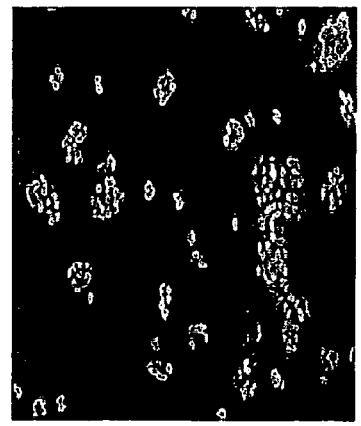
Figure 4C Formulation #5

AMPHIPHILIC NUCLEOTIDE COCHLEATE COMPOSITIONS AND METHODS OF USING THE SAME

RELATED APPLICATIONS

The present application is a continuation application of U.S. application Ser. No. 12/438,266, filed Feb. 20, 2009 and now abandoned, which, in turn, is a U.S. National Phase Application of PCT/US2007/018553, filed Aug. 22, 2007, which claims priority to U.S. Provisional Application Ser. No. 60/839,962 filed Aug. 23, 2006, and the entire contents of each of the aforementioned applications are hereby incorporated herein by reference.

FIELD OF THE INVENTION

The present application relates to cochleate compositions that include a nucleotide associated with a positively charged amphiphile and methods of making and using the same.

BACKGROUND OF THE INVENTION

Cochleate structures were first prepared by D. Papahadjopoulos as an intermediate in the preparation of large unilamellar vesicles. U.S. Pat. No. 4,078,052. COchleate compositions incorporating a variety of cargo moieties, methods of making and methods of using such cochleates have also been disclosed, e.g., in U.S. Pat. Nos. 5,840,707, 5,994,318, and 6,153,217, and International Application No. WO 04/091578. Specifically, U.S. Pat. No. 5,840,707 discloses protein-cochleates and polynucleotide-cochleates. The entire contents of these patents are incorporated by this reference.

Additionally, positively charged amphiphiles, e.g., esters of L-carnitine, have been used as transfection agents, as well as in the formation of liposomes for delivery of molecules, e.g., nucleotides. Specifically, U.S. Pat. No. 6,797,281 discloses compounds which are used as cationic lipids for delivery of pharmacologically active compounds, e.g., taxol liposomes and the like.

BRIEF SUMMARY OF THE INVENTION

The present invention is directed, at least in part, to nucleotide-cochleate compositions and methods of manufacture and administration. The composition may generally include a cochleate; and a nucleotide associated with the cochleate wherein the nucleotide is associated with a positively charged amphiphile.

In some embodiments, the positively charged amphiphile is a compound of formula (I):

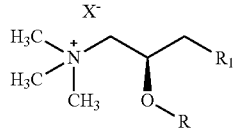
(I)

wherein:

R is selected from H, a C2-C26 acyl group and a C4-C26 aliphatic group;

$R_1$ is selected from

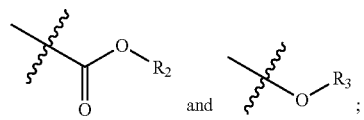

$R_2$ and $R_3$ are each independently a C4-C26 aliphatic group; optionally one or more of R, $R_2$ and $R_3$ can be:

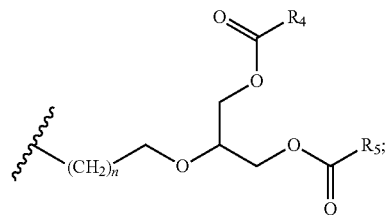

$R_4$ and $R_5$ are each independently a C3-C20 acyl group;

n is an integer from 1 to 3; and

X is an anion of a pharmaceutically acceptable compound.

In other embodiments, the positively charged amphiphile is a compound of formula (II):

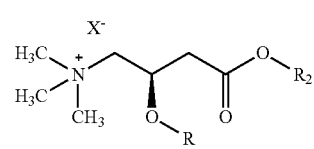
(II)

wherein:

R is selected from H, a C2-C26 acyl group and a C4-C26 aliphatic group;

$R_2$ is a C4-C26 aliphatic group;

optionally one or both of R and $R_2$ can be:

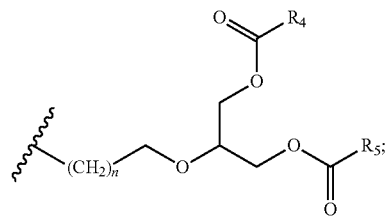

$R_4$ and $R_5$ are each independently a C3-C20 acyl group;

n is an integer from 1 to 3; and

X is an anion of a pharmaceutically acceptable compound.

In still other embodiments, the positively charged amphiphile is a compound of formula (III):

$$\text{(III)}$$

[Structure of formula (III): quaternary ammonium with H$_3$C, H$_3$C, CH$_3$ groups, N$^+$, X$^-$ counterion, connected to a chain with OR group, C(=O)O-(CH$_2$)$_n$-O-CH$_2$-CH(O-C(=O)R$_5$)-CH$_2$-O-C(=O)R$_4$]

wherein:
R is selected from a C2-C26 acyl group, a C4-C26 aliphatic group and H;
R$_4$ and R$_5$ are each independently a C3-C20 acyl group;
n is an integer from 1 to 3; and
X is an anion of a pharmaceutically acceptable compound.

In some embodiments, the present invention is also directed to methods of forming a nucleotide-cochleate composition. The method can generally include precipitating a liposome and a nucleotide to form a nucleotide-cochleate, wherein the nucleotide is associated with a positively charged amphiphile.

In other embodiments, the present invention is also directed to methods of administering a nucleotide to a host. The method generally includes administering a biologically effective amount of a nucleotide-cochleate composition to a host comprising a cochleate and a nucleotide associated with the cochleate, wherein the nucleotide is associated with a positively charged amphiphile.

In still other embodiments, the present invention is also directed to methods of treating a subject having a disease or disorder associated with expression of a target mRNA. The method generally includes administering to a subject a therapeutically effective amount of a nucleotide-cochleate composition, comprising a cochleate and a nucleotide directed against a target mRNA associated with a disease or disorder, wherein the nucleotide is associated with a positively charged amphiphile, such that the disease or disorder is treated.

BRIEF DESCRIPTION OF THE DRAWINGS

FIG. 1 is a schematic representation of the formation of exemplary cochleates of the present invention.

FIG. 2 depicts fluorescent and phase contrast images of the morphology of exemplary decoy cochleates.

FIGS. 4A-4E are images depicting cellular uptake of exemplary PS NFkB decoy cochleates.

DETAILED DESCRIPTION OF THE INVENTION

Figure 3A:
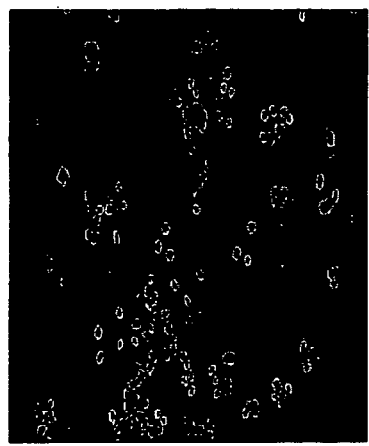
FIGS. 3A-3E are images depicting cellular uptake of exemplary H3 NFkB decoy cochleates.
Figure 3B:
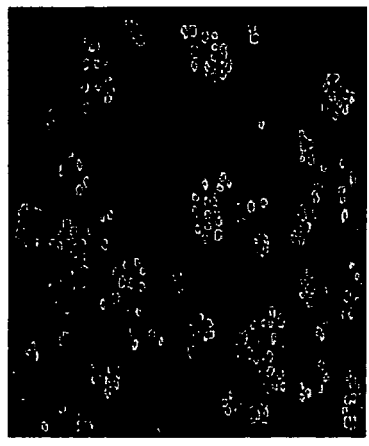
Figure 3E:
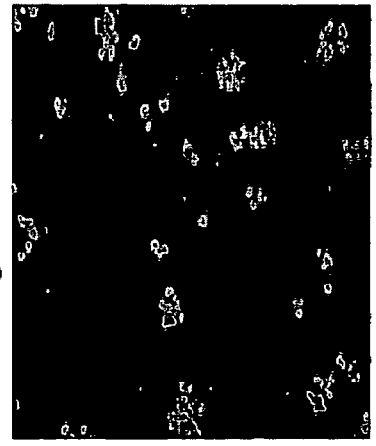
Figure 3D:
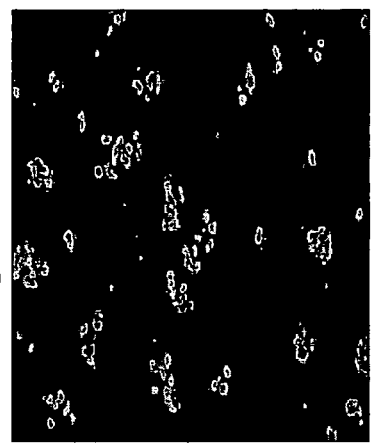
Figure 3C:
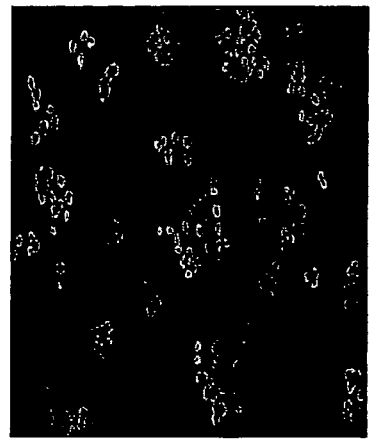

The present invention is based, at least in part, on the discovery that employing a nucleotide associated with a positively charged amphiphile may increase the association of the nucleotide with the cochleate and facilitate bioavailability of the nucleotide. Accordingly, in some embodiments, the present invention provides nucleotide-cochleate compositions which include a cochleate component and a nucleotide, wherein the nucleotide is associated with a positively charged amphiphile.

So that the invention may be more readily understood, certain terms are first defined.

The term "positively charged amphiphile" refers to an amphiphile, e.g., a molecule having a polar water-soluble group attached to a water-insoluble hydrocarbon chain. Exemplary positively charged amphiphiles include, but are not limited to esters and other derivatives of L-carnitine.

The term "associated with" refers to the interaction between one or more positive charges on a positively charged amphiphile and any full or partial negative charges on a nucleotide.

As used herein, the terms "cochleate," "lipid precipitate" and "precipitate" are used interchangeably to refer to a lipid precipitate component that generally includes alternating cationic and lipid bilayer sheets with little or no internal aqueous space, typically stacked and/or rolled up, wherein the cationic sheet is comprised of one or More multivalent cations. Additionally, the term "encochleated" means associated with the cochleate structure, e.g., by incorporation into the cationic sheet, and/or inclusion in the lipid bilayer.

As used herein, the term "multivalent cation" refers to a divalent cation or higher valency cation, or any compound that has at least two positive charges, including mineral cations such as calcium, barium, zinc, iron and magnesium and other elements, such as drugs and other compounds, capable of forming ions or other structures having multiple positive charges capable of chelating and bridging negatively charged lipids. Additionally or alternatively, the multivalent cation can include other multivalent cationic compounds, e.g., cationic or protonized cargo moieties.

The term "aliphatic group" includes organic moieties characterized by straight or branched-chains, typically having between 1 and 24 carbon atoms. In complex structures, the chains may be branched, bridged, or cross-linked. Aliphatic groups include aliphatic groups, alkenyl groups, alkynyl groups, and any combination thereof.

As used herein, "alkyl" groups include saturated hydrocarbons having one or more carbon atoms, e.g., between 1 and 24 carbon atoms, including straight-chain alkyl groups (e.g., methyl, ethyl, propyl, butyl, pentyl, hexyl, heptyl, octyl, nonyl, decyl, etc.) and branched-chain alkyl groups (isopropyl, tert-butyl, sec-butyl, isobutyl, etc.). It is to be understood that both straight-chain and branched-chain alkyl groups are encompassed by the term "alkyl".

In certain embodiments, a straight-chain or branched-chain alkyl group may have 30 or fewer carbon atoms in its backbone, e.g., $C_1$-$C_{30}$ for straight-chain or $C_3$-$C_{30}$ for branched-chain. In certain embodiments, a straight-chain or branched-chain alkyl group may have 20 or fewer carbon atoms in its backbone, e.g., $C_1$-$C_{20}$ for straight-chain or $C_3$-$C_{20}$ for branched-chain, and in more particular embodiments 18 or fewer. The term "C4-C24" as in "C4-C24 alkyl" means alkyl groups containing 4 to 24 carbon atoms.

The terms "alkenyl", "alkynyl" and "alkenylene" refer to unsaturated aliphatic groups analogous to alkyls, but which contain at least one double or triple carbon-carbon bond respectively.

The term "acyl" refers to a carbonyl group that is attached through its carbon atom to a hydrogen (i.e., a formyl) or an aliphatic group (e.g., acetyl), and the like.

The term "nucleoside" refers to a molecule having a purine or pyrimidine base covalently linked to a ribose or deoxyribose sugar. Exemplary nucleosides include adenosine, guanosine, cytidine, uridine and thymidine. The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "oligonucleotide" refers to a short sequence of nucleotides and/or nucleotide analogs. The term "RNA analog" refers to an polynucleotide (e.g., a chemically synthesized polynucleotide) having at least one altered or modified nucleotide as compared to a corresponding unaltered or unmodified RNA, but retaining the same or similar nature or function as the corresponding unaltered or unmodified RNA. The oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. In some embodiments, RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, an "identical" oligonucleotide has the same sequence as the reference nucleotide subsequence to which the oligonucleotide is being compared. An "exactly complementary" oligonucleotide refers to an oligonucleotide whose complement has the same sequence as the reference nucleotide subsequence to which the oligonucleotide is being compared. A "substantially complementary" and a "substantially identical" oligonucleotide have the ability to specifically hybridize to a reference gene, DNA, cDNA, or mRNA, and its exact complement.

An "antisense" oligonucleotide is an oligonucleotide that is substantially complementary to a target nucleotide sequence and has the ability to specifically hybridize to the target nucleotide sequence.

The term "RNA" or "RNA molecule" or "ribonucleic acid molecule" refers to a polymer of ribonucleotides. The term "DNA" or "DNA molecule" or "deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "RNA interference" ("RNAi") refers to a selective intracellular degradation of RNA to mediate, reduce or silence the expression of a target gene.

As used herein, the term "small interfering RNA" ("siRNA") (also referred to in the art as "short interfering RNAs") refers to a double stranded RNA (or RNA analog) comprising between about 10-50 nucleotides (or nucleotide analogs) which is capable of directing or mediating RNA interference.

As used herein, the term "short double stranded DNA" refers to a double stranded DNA (or DNA analog) comprising less than about 50 nucleotides (or nucleotide analogs).

"Morpholino oligonucleotides" and "morpholinos" are used interchangeably, and refer to oligonucleotides having a morpholino backbone. Morpholinos function by an RNase H-independent mechanism and are soluble in aqueous solutions, with most being freely soluble at mM concentrations (typically 10 mg/ml to over 100 mg/ml). Morpholinos have high affinity for RNA and efficiently invade even quite stable secondary structures in mRNAs, which results in effective and predictable targeting essentially anywhere from the 5'-cap to about +25 of the protein coding region of mRNAs. Morpholinos are free of significant non-antisense effects while the alternative phosphorothioates are plagued by a host of well-documented non-antisense effects. Morpholinos include a morpholine backbone, which is not recognized by nucleases and therefore is stable in the cell compared to phosphorothioates, which typically are degraded in biological systems in a matter of hours. Consequently, considerably fewer morpholinos are required (approximately 100× less) to achieve similar antisense effects. Morpholinos can also be superior to phosphorothioates because targeting is more predictable, the activity in cells is more reliable, and the sequence specificity is superior. Summerton, *Biochimica et Biophysica Acta* 1489: 141-158 (1999). Morpholinos can be designed and prepared according to known methods. E.g., Summerton and Weller, Antisense and Nucleic Acid Drug Development 7 187-195 (1997).

As used herein, the terms "ribozyme" and "RNA enzyme" are used interchangeably to refer to RNA molecules that catalyze chemical reactions. In addition to catalyzing cleavage of themselves and/or other RNAs, ribozymes may also catalyze the aminotransferase activity of the ribosome. Ribozymes, although quite rare in cells, often have essential functions, e.g., a role in the ribosomal translation of RNA into proteins. Known ribozymes include, but are not limited to RNase P, Group I and Group II introns, leadzyme, hairpin ribozyme, hammerhead ribozyme, hepatitis delta virus ribozyme, and tetrahymena ribozyme. Additionally, ribozymes may be made synthetically, e.g., while maintaining good enzymatic activity. Synthetic ribozymes may have structures similar to naturally occurring ribozymes or may have novel structures.

The term "aptamer," as used herein, refers generally to single-stranded DNA and RNA molecules that bind target molecules with high affinity and specificity. Aptamers may be selected in vitro from populations of random sequences that recognize specific ligands by forming binding pockets. Aptamers can be chemically synthesized and, although single-stranded, normally have complex three-dimensional shapes. Generally, an aptamer domain on an RNA enzyme, or ribozyme, modulates the activity of the ribozyme. In a manner similar to antibodies, when the shape of the aptamer corresponds to the shape of a target protein, a strongly bound complex can be formed. These aptamers may have potential in targeted delivery of drugs, either through direct conjugation of the drug to an aptamer, or through drug encapsulation in a vesicle, e.g., a liposome, which is coated in an aptamer. Accordingly, in one embodiment, the nucleotides employed in the compositions of the present invention are aptamers. The aptamers may be contained at least partially within the cochleate structure. Alternatively, the aptamers may be coated on the cochleate. The aptamer-cochleate may include additional cargo moieties for targeted delivery.

As used herein, the term "transcription factor decoys" refers to nucleotides, generally oligodeoxynucleotides (ODNs), which are used to inhibit specific transcription factors, e.g., in cell culture. Transcription factor proteins bind specific sequences found in the promoter regions of target genes whose expression they then regulate. These binding sequences are generally 6-10 base pairs in length and are occasionally found in multiple copies within the promoter regions of target genes. A cell can be flooded with transcription factor decoys, which compete for binding of the transcription factor with sequences in target genes. The decoys have the potential to alter the binding and function of the transcription factor, thus regulating the expression of the target gene. At higher concentrations, transcription factor decoys may completely block transcription factor function. Exemplary transcription factor decoys are described, e.g., in Morishita, R., et al., *Circ Res,* 82, 1023-1028 (1998) and Mann, M. J. and Dzau, V. J., *J. Clin. Invest.,* 106, 1071-1075 (2000). Additional exemplary transcription factor decoys are E2F Decoys, which are DNA-based competitive inhibitor, useful, e.g., in the prevention of bypass graft failure and NF-kB Decoys, useful, e.g., in the treatment of Atopic Dermatitis and other inflammation indications.

A nucleotide "that mediates RNAi against a target mRNA" refers to a nucleotide including a sequence sufficiently complementary to a target RNA (e.g. mRNA or RNA that can be spliced to produce one or more mRNAs) to trigger the destruction of the target mRNA by the RNAi machinery or process or to interfere with translation of the mRNA into a protein.

The term "nucleotide analog" or "altered nucleotide" or "modified nucleotide" refers to a non-standard nucleotide, including non-naturally occurring ribonucleotides or deoxyribonucleotides. In some embodiments, nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2'OH-group may be replaced by a group selected from H, OR, R, F, Cl, Br, I, SH, SR, $NH_2$, NHR, $NR_2$, COOR, or OR, wherein R is substituted or unsubstituted C1-C6 alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11 (5): 317-25, Vorobjev et al. Antisense Nucleic Acid Drug Dev. 2001 Apr. 11.2):77-85, and U.S. Pat. No. 5,684,143. In some embodiments, certain of the above-referenced modifications (e.g., phosphate group modifications) decrease the rate of hydrolysis of, for example, polynucleotides comprising said analogs in vivo or in vivo.

A gene or mRNA "involved" in or "associated with" a disorder includes a gene or mRNA, the normal or aberrant expression or function of which effects or causes a disease or disorder or at least one symptom of said disease or disorder.

The phrase "examining the function of a target mRNA" refers to examining or studying the expression, activity, function or phenotype arising therefrom, in the host cell, tissue or organism.

Cochleates

Cochleates and methods for making and using have been disclosed, e.g., in U.S. Pat. Nos. 5,999,318 and 6,592,894. Cochleate delivery vehicles are stable lipid-cation precipitates that can be composed of simple, naturally occurring materials, e.g., phosphatidylserine, and calcium. Mixtures of naturally occurring molecules (e.g., soy lipids) and/or synthetic or modified lipids can be utilized.

The cochleate structure provides protection from degradation for associated "encochleated" moieties. Divalent cation concentrations in vivo in serum and mucosal secretions are such that the cochleate structure is maintained. Hence, the majority of cochleate-associated molecules, e.g., cargo moieties, are present in the inner layers of a primarily solid, non-aqueous, stable, impermeable structure. Since the cochleate structure includes a series of solid layers, components within the interior of the cochleate structure remain substantially intact, even though the outer layers of the cochleate may be exposed to harsh environmental conditions or enzymes.

The cochleate interior is primarily free of water and resistant to penetration by oxygen. Oxygen and water are primarily responsible for the decomposition and degradation of molecules which can lead to reduced shelf-life. Accordingly, encochleation can also impart extensive shelf-life stability to encochleated nucleotides.

With respect to storage, cochleates can be stored in cation-containing buffer, or lyophilized or otherwise converted to a powder, and stored at room temperature. If desired, the cochleates also can be reconstituted with liquid prior to administration. Cochleate preparations have been shown to be stable for more than two years at 4° C. in a cation-containing buffer, and at least one year as a lyophilized powder at room temperature.

In one embodiment, the cochleate comprises a negatively charged lipid component and a multivalent cation component. The lipid employed in the present invention may include one or more negatively charged lipids. As used herein, the term "negatively charged lipid" includes lipids having a head group bearing a formal negative charge in aqueous solution at an acidic, basic or physiological pH, and also includes lipids having a zwitterionic head group.

In one embodiment, the lipid is a mixture of lipids, comprising at least 75% negatively charged lipid. In another embodiment, the lipid includes at least 85% negatively charged lipid. In other embodiments, the lipid includes at least 90%, 95% or even 99% negatively charged lipid. All ranges and values between 60% and 100% negatively charged lipid are meant to be encompassed herein.

The negatively charged lipid can include soy-based lipids. In some embodiments, the lipid includes phospholipids, such as soy-based phospholipids. The negatively charged lipid can include phosphotidyl serine (PS), dioleoylphosphatidylserine (DOPS), phosphatidic acid (PA), phosphatidylinositol (PI), and/or phosphatidyl glycerol (PG) and or a mixture of one or more of these lipids with other lipids. Additionally or alternatively, the lipid can include phosphatidylcholine (PC), phosphatidylethanolamine (PE), diphosphotidylglycerol (DPG), dioleoyl phosphatidic acid (DOPA), distearoyl phosphatidylserine (DSPS), dimyristoyl phosphatidylserine (DMFS), dipalmitoyl phosphatidylgycerol (DPPG) and the like.

The lipids can be natural or synthetic. For example, the lipid can include esterified fatty acid acyl chains, or organic chains attached by non-ester linkages such as ether linkages (as described in U.S. Pat. No. 5,956,159), disulfide linkages, and their analogs.

In one embodiment the lipid chains are from about 6 to about 26 carbon atoms, and the lipid chains can be saturated or unsaturated. Fatty acyl lipid chains useful in the present invention include, but are not limited to, n-tetradecanoic, n-hexadecanoic acid, n-octadecanoic acid, n-eicosanoic acid, n-docosanoic acid, n-tetracosanoic acid, n-hexacosanoic acid, cis-9-hexadecenoic acid, cis-9-octadecenoic acid, cis, cis-9,12-octadecedienoic acid, all-cis-9,12,15-octadecetrienoic acid, all-cis-5,8,11,14-eicosatetraenoic acid, all-cis-4,7,10,13,16,19-docosahexaenoic acid, 2,4,6,8-tetramethyl decanoic acid, and lactobacillic acid, and the like.

The cochleates of the invention can further include additional compounds known to be used in lipid preparations, e.g., cholesterol and/or pegylated lipid. Pegylated lipid includes lipids covalently linked to polymers of polyethylene glycol (PEG). PEG's are conventionally classified by their molecular weight, thus PEG 6,000 MW, e.g., has a molecular weight of about 6000. Adding pegylated lipid generally will result in an increase of the amount of compound (e.g., peptide, nucleotide, and nutrient) that can be incorporated into the cochleate. An exemplary pegylated lipid is dipalmitoylphosphatidylehtanolamine (DPPE) bearing PEG 5,000 MW.

The nucleotide-cochleate compositions of the present invention can be provided in a variety of forms (e.g. powder, liquid, suspension) with or without additional components. Suitable forms and additives, excipients, carriers and the like are known in the art.

Positively Charged Amphiphiles

In some embodiments, the present invention is directed to cochleates which include a cochleate component and a nucleotide, wherein the nucleotide is associated with a positively charged amphiphile.

Without wishing to be bound by any particular theory, it is believed that enhanced binding of the nucleotide and the liposome and/or cochleates may be achieved by first forming an association between the nucleotide and a positively charged amphiphile. The transfection potential of DNA complexed with certain positively charged amphiphiles has been described, e.g., in U.S. Pat. No. 6,797,281, the contents of which are incorporated herein in its entirety by this reference. However, in general, increased transfection rates have been coupled with increased toxicity. Bogden et al., *AACS Pharm-Sci* 4(2) (2002).

The addition of a positively charged amphiphile to a nucleotide cochleate may be advantageous, e.g., in delivery of the nucleotide. For example, it is believed that encochleated nucleotides which are associated with positively charged amphiphiles, e.g., palmitoyl L-carnitine chloride undecyl ester, may improve transfection into cells without the associated toxicity generally observed. Accordingly, in some embodiments, cochleates including nucleotides associated with positively charged amphiphiles have significantly no toxicity or undetectable toxicity in vivo and/or in vitro. Moreover, associating the nucleotide to a positively charged amphiphile may also be advantageous for facilitating the transfer of the nucleotide across membranes subsequent to administration.

The ratios of positively charged amphiphile to nucleotide may vary. In some embodiments, N to P ratios (nitrogen in the positively charged amphiphile to phosphate in the nucleotide) may vary from between about 0.5 to about 20. In certain embodiments, the N to P ratio is between about 4 and about 8.

In some embodiments, the positively charged amphiphile is a compound of formula (I):

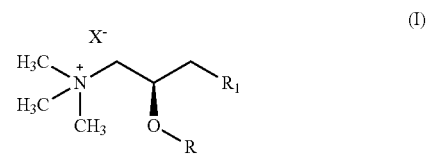

wherein:

R is selected from H, a C2-C26 acyl group and a C4-C26 aliphatic group;

$R_1$ is selected from

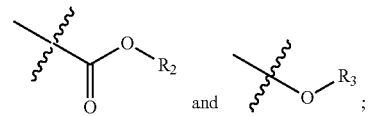

$R_2$ and $R_3$ are each independently a C4-C26 aliphatic group;

optionally one or more of R, $R_2$ and $R_3$ can be:

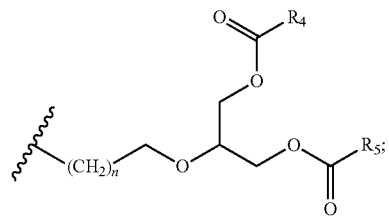

$R_4$ and $R_5$ are each independently a C3-C20 acyl group;

n is an integer from 1 to 3; and

X is an anion of a pharmaceutically acceptable compound.

For example, in some embodiments, R is a C8-C20 acyl group, e.g., nonanoyl, dodecanoyl, myristoyl, palmitoyl, steroyl or oleoyl. In other embodiments, R is a C8-C20 aliphatic group, e.g., oleyl, nonyl, undecyl, tetradecyl, or hexadecyl.

In some embodiments, $R_1$ is

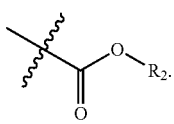

In some embodiments, $R_2$ is a C8-C20 aliphatic group, e.g., oleyl, nonyl, undecyl, tetradecyl, or hexadecyl. In other embodiments, $R_1$ is

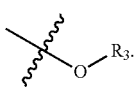

In some embodiments, $R_3$ is a C8-C20 aliphatic group, e.g., oleyl, nonyl, undecyl, tetradecyl, or hexadecyl.

In some embodiments, $R_2$ is

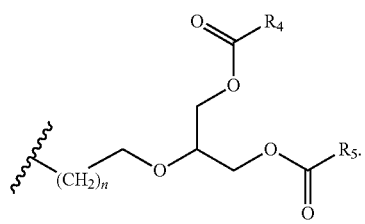

In some embodiments, $R_4$ and $R_5$ are each independently a C6-C18 acyl group, e.g., hexanoyl, undecanoyl, myristoyl, palmitoyl or oleoyl. In some embodiments, e.g., when $R_2$ is

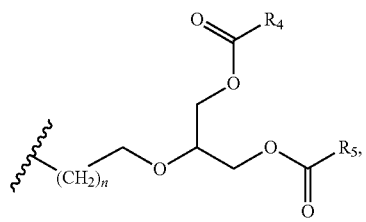

R is a C2-C6 acyl group, e.g., acetyl, propionyl, butyryl, valeryl and isovaleryl.

In other embodiments, the positively charged amphiphile is a compound of formula (II):

(II)

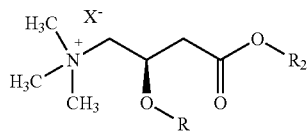

wherein:
R is selected from H, a C2-C26 acyl group and a C4-C26 aliphatic group;
$R_2$ is a C4-C26 aliphatic group;

optionally one or both of R and $R_2$ can be:

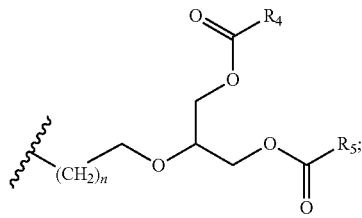

$R_4$ and $R_5$ are each independently a C3-C20 acyl group;
n is an integer from 1 to 3; and
X is an anion of a pharmaceutically acceptable compound.

In some embodiments, R is a C8-C20 acyl group, e.g., nonanoyl, dodecanoyl, myristoyl, palmitoyl, steroyl or oleoyl. In other embodiments, R is a C8-C20 aliphatic group, e.g., oleyl, nonyl, undecyl, tetradecyl, or hexadecyl.

In some embodiments, $R_2$ is a C8-C20 aliphatic group, e.g., oleyl, nonyl, undecyl, tetradecyl, or hexadecyl. In other embodiments, $R_2$ is

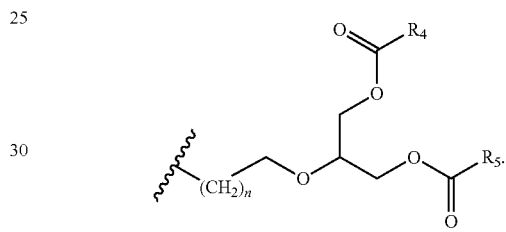

In some embodiments, $R_4$ and $R_5$ are each independently a C6-C18 acyl group, e.g., hexanoyl, undecanoyl, myristoyl, palmitoyl or oleoyl. In some embodiments, e.g., when $R_2$ is R is a $C_2$-$C_6$ acyl group, e.g., acetyl, propionyl, butyryl, valeryl and isovaleryl.

In still other embodiments, the positively charged amphiphile is a compound of formula (III):

(III)

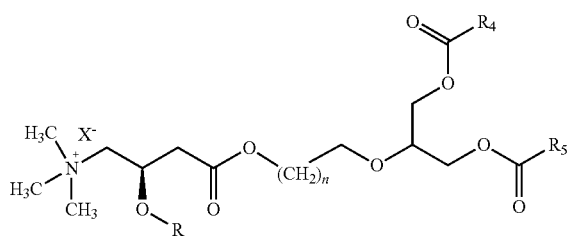

wherein:
R is selected from a C2-C26 acyl group, a C4-C26 aliphatic group and H;
$R_4$ and $R_5$ are each independently a C3-C20 acyl group;
n is an integer from 1 to 3; and
X is an anion of a pharmaceutically acceptable compound.

In some embodiments, R is a C8-C20 acyl group, e.g., nonanoyl, dodecanoyl, myristoyl, palmitoyl, steroyl or oleoyl. In other embodiments, R is a C8-C20 aliphatic group, e.g., oleyl, nonyl, undecyl, tetradecyl, or hexadecyl. In other embodiments, R is a C2-C6 acyl group, e.g., acetyl, propionyl, butyryl, valeryl and isovaleryl.

In some embodiments, $R_4$ and $R_5$ are each independently a C6-C18 acyl group, e.g., hexanoyl, undecanoyl, myristoyl, palmitoyl or oleoyl.

Examples of anions of pharmacologically acceptable acids include, but are not limited to chloride, bromide, iodide, aspartate, acid aspartate, citrate, acid citrate, tartrate, acid tartrate, phosphate, acid phosphate, fumarate, acid fumarate, glycerophosphate, glucose phosphate, lactate, maleate, acid maleate, mucate, orotate, oxalate, acid oxalate, sulphate, acid sulphate, trichloroacetate, trifluoroacetate, methane sulphonate, pamoate and acid pamoate.

Examples of positively charged amphiphiles according to the invention include, but are not limited to: N-[1-(2,3-dioleyloxy)propyl]-N,N,N-trimethylammonium chloride (DOTMA), ester of L-carnitine bromide with 2-hydroxyacetyl-1,3-dipalmitoyl glycerol, ester of acetyl L-carnitine bromide with 2-hydroxyacetyl-1,3-dipalmitoyl glycerol, ester of propionyl L-carnitine bromide with 2-hydroxyacetyl-1,3-dipalmitoyl glycerol, ester of isobutyryl L-carnitine bromide with 2-hydroxyacetyl-1,3-dipalmitoyl glycerol, ester of isovaleryl L-carnitine bromide with 2-hydroxyacetyl-1,3-dipalmitoyl glycerol, ester of L-carnitine bromide with 1,3-dihexanoyl-2-hydroxycetyl glycerol, ester of acetyl L-carnitine bromide with 1,3-dihexanoyl-2-hydroxyacetyl glycerol, ester of propionyl L-carnitine bromide with 1,3-dihexanoyl-2-hydroxyacetyl glycerol, isovaleryl L-carnitine undecyl ester, isobutyryl L-carnitine undecyl ester, palmitoyl L-carnitine chloride undecyl ester, stearoyl L-carnitine chloride undecyl ester, stearoyl L-carnitine chloride tetradecyl ester, palmitoyl L-carnitine chloride tetradecyl ester, miristoyl L-carnitine chloride tetradecyl ester, palmitoyl L-carnitine bromide hexadecyl ester, and oleyl L-carnitine chloride oleyl ester. In some embodiments, the positively charged amphiphile is an L-carnitine derivative. In other embodiments, the positively charged amphiphile is a compound described in U.S. Pat. No. 6,797,281.

Positively charged amphiphiles may also be combined in some ratio with additional lipids or amphiphiles. In some embodiments, the additional lipids or amphiphiles are neutral. For example, the present invention includes cochleates which include a negatively charged lipid, an siRNA associated with Lipofectin, and a multivalent cation.

In some embodiments, the positively charged amphiphile does not include protamine, polyethylenimine (PEI), Lipofectamine, polyvinylamine, spermine, spermidine, histamine, vitamin E or cationic lipid.

Nucleotides

In certain embodiments, the present invention features encochleated nucleotide compositions. The nucleotide-cochleate compositions generally include a cochleate, and a nucleotide as described herein associated with the cochleate, e.g., a nucleotide that is bound to a lipophilic tail via a linker. The present invention also includes methods (e.g., research and/or therapeutic methods) for using nucleotide-cochleates.

In some embodiments, the nucleotide is an siRNA. In other embodiments, the nucleotide is a morpholino oligonucleotide. Morpholino oligonucleotides suitable for use in the present invention include antisense morpholino oligonucleotides. Although a typical morpholino may be uncharged, the skilled artisan would be able to place a charge on the morpholino using no more than routine experimentation, e.g., changing the pH. The charge would then be able to interact with the positively charged amphiphile as described herein. In still other embodiments, the nucleotide is a short double-stranded DNA. In still other embodiments, the nucleotide is a ribozyme. In yet other embodiments, the nucleotide is an aptamer. In still other embodiments, the nucleotide is a transcription factor decoy. In certain embodiments of the present invention, the nucleotide is not DNA.

The nucleotides of the present invention can be between about 7 and 100 nucleotides long, between 10 and 50, between 20 and 35, and between 15 and 30 nucleotides long. The nucleotides of the present invention can be 15, 16, 17, 18, 19, 20, 21, 22, 23, 24, 25, 26, 27, 28, 29 or 30 nucleotides in length. For example, in some embodiments, a morpholino oligonucleotide is between about 18 and about 25 nucleotides long. In other embodiments, an siRNA has a length of from about 21-23 nucleotides.

The nucleotides of the invention, e.g., siRNAs or morpholinos, can mediate RNA interference against a target gene. That is, in some embodiments, the nucleotide has a sequence sufficiently complementary to a target RNA (e.g. mRNA or RNA that can be spliced to produce one or more mRNAs) associated with a target gene to trigger the destruction of the target mRNA by the RNAi machinery or process. The nucleotide can be designed such that every residue is complementary to a residue in the target molecule. Alternatively, one or more substitutions can be made within the molecule to increase stability and/or enhance processing activity of said molecule. Substitutions can be made within the strand or can be made to residues at the ends of the strand. In some embodiments, the nucleotides mediate inhibition of translation of a target mRNA or are directed against the synthesis of a protein.

The target mRNA cleavage reaction guided by nucleotides of the present invention is sequence specific. In some embodiments, nucleotides containing a sequence identical to a portion of the target gene may be preferred for inhibition. However, 100% sequence identity between the nucleotide and the target gene is not required to practice the present invention. Sequence variations can be tolerated including those that might be expected due to genetic mutation, strain polymorphism, or evolutionary divergence. For example, nucleotide sequences with insertions, deletions, and single point mutations relative to the target sequence have also been found to be effective for inhibition. Alternatively, nucleotide sequences with nucleotide analog substitutions or insertions can be effective for inhibition. Accordingly, in one embodiment, the nucleotide of the present invention is identical to a reference nucleotide subsequence. In another embodiment, the nucleotide is exactly complementary to a reference nucleotide subsequence. In still another embodiment, the nucleotide is substantially complementary to a reference nucleotide subsequence.

Moreover, not all positions of a nucleotide contribute equally to target recognition. For example, mismatches in the center of an siRNA are most critical and essentially abolish target RNA cleavage. In contrast, the 3' nucleotides of an siRNA do not contribute significantly to specificity of the target recognition. Generally, residues at the 3' end of the siRNA sequence which is complementary to the target RNA (e.g., the guide sequence) are not critical for target RNA cleavage.

Sequence identity may readily be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A non-limiting example of a local alignment algorithm utilized for the comparison of sequences is the algorithm of Karlin and Altschul (1990) *Proc. Natl. Acad. Sci.* USA 87:2264-68, modified as in Karlin and Altschul (1993) *Proc. Natl. Acad. Sci.* USA 90:5873. Such an algorithm is incorporated into the BLAST programs (version 2.0) of Altschul, et al. (I 990) *J Mol. Biol.* 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) *Nucleic Acids Res.* 25(17):3389. In another embodiment, the alignment is optimized by introducing appropriate gaps and percent identity is determined over the entire length of the sequences aligned (i.e., a global alignment). A non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Greater than 90% sequence identity, e.g., 91%, 92%, 93%, 94%, 95%, 96%, 97%, 98%, 99% or even 100% sequence identity, between the nucleotide and the portion of the target mRNA is preferred in certain embodiments. Alternatively, the nucleotide may be defined functionally as a nucleotide sequence (or oligonucleotide sequence) that is capable of hybridizing with a portion of the target mRNA transcript (e.g., 400 mM NaCl, 40 mM PIPES pH 6.4, 1 mM EDTA, 50° C. or 70° C. hybridization for 12-16 hours; followed by washing). Additional hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6($\log_{10}$[Na+])+0.41 (% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold 15 Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference. The length of the identical nucleotide sequences may be at least about or about equal to 10, 12, 15, 17, 20, 22, 25, 27, 30, 32, 35, 37, 40, 42, 45, 47 or 50 bases.

In one embodiment, the nucleotides of the present invention are modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference. For example, the absence of a 2'-hydroxyl may significantly enhance the nuclease resistance of the nucleotides in tissue culture medium.

In another embodiment of the present invention the nucleotide may contain at least one modified nucleotide analogue. The nucleotide analogues may be located at positions where the target-specific activity, e.g., the RNAi mediating activity is not substantially effected, e.g., in a region at the 5'-end and/or the 3'-end of the RNA molecule. Particularly, the ends may be stabilized by incorporating modified nucleotide analogues.

Nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In certain backbone-modified ribonucleotides the phosphoester group connecting to adjacent ribonucleotides is replaced by a modified group, e.g., of phosphothioate group. In certain sugar modified ribonucleotides, the 2'-OH-group is replaced by a group selected from H, OR, R, halo, SH, SR, $NH_2$, NHR, $NR_2$ or $NO_2$, wherein R is C1-C6 alkyl, alkenyl or alkynyl and halo is F, Cl, Br or I.

Nucleotide analogues also include nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

Nucleotides may be produced enzymatically or by partial/total organic synthesis and any modified ribonucleotide can be introduced by in vitro enzymatic or organic synthesis. In one embodiment, nucleotides of the present invention are prepared chemically. Methods of synthesizing RNA molecules are known in the art, in particular, the chemical synthesis methods as described in Verina and Eckstein (1998),

*Annual Rev. Biochem.* 67:99. In another embodiment, nucleotides of the present invention are prepared enzymatically. For example, nucleotides can be prepared by enzymatic processing of a long, double-stranded RNA having sufficient complementarity to the desired target mRNA. Processing of long RNA can be accomplished in vitro, for example, using appropriate cellular lysates and siRNAs or morpholinos can be subsequently purified by gel electrophoresis or gel filtration. Nucleotides can then be denatured according to art-recognized methodologies. In an exemplary embodiment, nucleotides can be purified from a mixture by extraction with a solvent or resin, precipitation, electrophoresis, chromatography, or a combination thereof. Alternatively, the nucleotides may be used with no or a minimum of purification to avoid losses due to sample processing.

In one embodiment, nucleotides of the present invention are synthesized either in vivo, in situ, or in vitro. Endogenous RNA polymerase of the cell may mediate transcription in vivo or in situ, or cloned RNA polymerase can be used for transcription in vivo or in vivo. For transcription from a transgene in vivo or an expression construct, a regulatory region (e.g., promoter, enhancer, silencer, splice donor and acceptor, polyadenylation) may be used to transcribe the morpholinos. Inhibition may be targeted by specific transcription in an organ, tissue, or cell type; stimulation of an environmental condition (e.g., infection, stress, temperature, chemical inducers); and/or engineering transcription at a developmental stage or age. A transgenic organism that expresses a nucleotide of the present invention from a recombinant construct may be produced by introducing the construct into a zygote, an embryonic stem cell, or another multipotent cell derived from the appropriate organism.

Alternatively, nucleotides, e.g., siRNAs, can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) *Methods Enzymol.* 180:51-62). The RNA may be dried for storage or dissolved in an aqueous solution. The solution may contain buffers or salts to inhibit annealing, and/or promote stabilization of the double strands.

Commercially available design tools and kits, such as those available from Ambion, Inc. (Austin, Tex.), and the Whitehead Institute of Biomedical Research at MIT (Cambridge, Mass.) allow for the design and production of siRNA. By way of example, a desired mRNA sequence can be entered into a sequence program that will generate sense and antisense target strand sequences. These sequences can then be entered into a program that determines the sense and antisense siRNA oligonucleotide templates. The programs can also be used to add, e.g., hairpin inserts or T1 promoter primer sequences. Kits also can then be employed to build siRNA expression cassettes.

In some embodiments, the target mRNA expresses a protein which can be, but is not limited to a cancer protein, a virus protein, an HIV protein, a fungus protein, a bacterial protein, an abnormal cellular protein, and/or a normal cellular protein. For example, in one embodiment, the target mRNA of the invention specifies the amino acid sequence of at least one protein such as a cellular protein (e.g., a nuclear, cytoplasmic, transmembrane, or membrane-associated protein). In another embodiment, the target mRNA of the invention specifies the amino acid sequence of an extracellular protein (e.g., an extracellular matrix protein or secreted protein). As used herein, the phrase "specifies the amino acid sequence" of a protein means that the mRNA sequence is translated into the amino acid sequence according to the rules of the genetic code. The following classes of proteins are listed for illustrative purposes: developmental proteins (e.g., adhesion molecules, cyclin kinase inhibitors, Wnt family members, Pax family members, Winged helix family members, Hox family members, cytokines/lymphokines and their receptors; growth/differentiation factors and their receptors, neurotransmitters and their receptors); oncogene-encoded proteins (e.g., ABLI, BCLI, BCL2, BCL6, CBFA2. CBL, CSFIR, ERBA, ERBB, EBRB2, ETSI, ETSI, ETV6. FGR, FOS, FYN, HCR, HRAS, JUN, KRAS, LCK, LYN, MDM2, MLL, MYB, MYC, MYCLI, MYCN, NRAS, PIM 1, PML, RET, SRC, TALI, TCL3, and YES); tumor suppressor proteins (e.g., APC, BRCA1, BRCA2, MADH4, MCC, NF 1, NF2, RB 1, TP53, and WTI); and enzymes (e.g., ACC synthases and oxidases, ACP desaturases and hydroxylases, ADPglucose pyrophorylases, acetylases and deacetylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases), proteins involved in tumor growth (including vascularization) or in metastatic activity or potential, including cell surface receptors and ligands as well as secreted proteins, cell cycle regulatory, gene regulatory, and apoptosis regulatory proteins, immune response, inflammation, complement, or clotting regulatory proteins.

As used herein, the term "oncogene" refers to a gene which stimulates cell growth and, when its level of expression in the cell is reduced, the rate of cell growth is reduced or the cell becomes quiescent. In the context of the present invention, oncogenes include intracellular proteins, as well as extracellular growth factors which may stimulate cell proliferation through autocrine or paracrine function. Examples of human oncogenes against which nucleotide constructs, e.g., siRNA or morpholino constructs can be designed include c-myc, c-myb, mdm2, PKA-I (protein kinase A type I), Abl-1, Bcl2, Ras, c-Raf kinase, CDC25 phosphatases, cyclins, cyclin dependent kinases (cdks), telomerase, PDGF/sis, erb-B, fos, jun, mos, and src, to name but a few. In the context of the present invention, oncogenes also include a fusion gene resulted from chromosomal translocation, for example, the Bcr/Abl fusion oncogene.

Further proteins include cyclin dependent kinases, c-myb, c-myc, proliferating cell nuclear antigen (PCNA), transforming growth factor-beta (TGF-beta), and transcription factors nuclear factor kappaB (NF-.kappa.B), E2F, HER-2/neu, PICA, TGF-alpha, EGFR, TGF-beta, IGFIR, P12, MDM2, BRCA, Bcl-2, VEGF, MDR, ferritin, transferrin receptor, IRE, C-fos, HSP27, C-raf and metallothionein genes.

The nucleotides employed in the present invention can be directed against the synthesis of one or more proteins. Additionally or alternatively, there can be more than one nucleotide directed against a protein, e.g., duplicate nucleotides or nucleotides that correspond to overlapping or non-overlapping target sequences against the same target protein. Additionally, several nucleotides directed against several proteins can be employed. Accordingly, in one embodiment two, three, four or any plurality of nucleotides against the same target mRNA can be including in the cochleate compositions of the invention. Alternatively, the nucleotides can be directed against structural or regulatory RNA molecules that do not code for proteins.

In certain embodiments of the invention, the target mRNA molecule of the invention specifies the amino acid sequence of a protein associated with a pathological condition. For example, the protein may be a pathogen-associated protein (e.g., a viral protein involved in immunosuppression or immunoavoidance of the host, replication of the pathogen, transmission of the pathogen, or maintenance of the infection), or a host protein which facilitates entry of the pathogen into the host, drug metabolism by the pathogen or host, replication or integration of the pathogen's genome, establishment or spread of infection in the host, or assembly of the next generation of pathogen. Alternatively, the protein may be a tumor-associated protein or an autoimmune disease-associated protein.

In one embodiment, the target mRNA molecule of the invention specifies the amino acid sequence of an endogenous protein (i.e. a protein present in the genome of a cell or organism). In another embodiment, the target mRNA molecule of the invention specifies the amino acid sequence of a heterologous protein expressed in a recombinant cell or a genetically altered organism. In another embodiment, the target mRNA molecule of the invention specifies the amino acid sequence of a protein encoded by a transgene (i.e., a gene construct inserted at an ectopic site in the genome of the cell). In yet another embodiment, the target mRNA molecule of the invention specifies the amino acid sequence of a protein encoded by a pathogen genome which is capable of infecting a cell or an organism from which the cell is derived.

By inhibiting the expression of such proteins, valuable information regarding the function of said proteins and therapeutic benefits which may be obtained from said inhibition may be obtained.

Accordingly, in one embodiment, the nucleotide-cochleate compositions of the present invention can be utilized in studies of mammalian cells to clarify the role of specific structural and catalytic proteins. In another embodiment, they can be used in a therapeutic application to specifically target pathogenic organisms, including fungi, bacteria, and viruses.

Methods of Forming Cochleates

In one embodiment, the invention provides methods for forming cochleates. Any known method can be used to form cochleates, including but not limited to those described in U.S. Pat. Nos. 5,994,318 and 6,153,217, the entire disclosures of which are incorporated herein by this reference.

In one embodiment, the method generally includes introducing a nucleotide associated with a positively charged amphiphile to a lipid, and precipitating to form a cochleate. Additionally or alternatively, the method generally includes introducing a nucleotide to a lipid, adding a positively charged amphiphile, and precipitating to form a cochleate.

The step of introducing a nucleotide to a lipid can be achieved in a variety of ways, all of which are encompassed within the scope of the present invention. For example, the nucleotide can be in a solvent, a buffer, an aqueous solution, etc. In some embodiments, the lipid is in a liposomal suspension, e.g., an aqueous liposomal suspension.

Utilizing the methods of the invention a wide range of lipid to nucleotide ratios can be achieved. Different ratios can have varying biological activity. The amount of nucleotide incorporated into the cochleates can be varied as desired. The optimal lipid:nucleotide ratio for a desired purpose can readily be determined without undue experimentation. The cochleates can be administered to the targeted host to ascertain the nature and tenor of the biologic response to the administered cochleates. It is evident that the optimized ratio for any one use may range from a high ratio to a low ratio to obtain maximal results. All ratios disclosed herein are w/w, unless otherwise indicated. In one embodiment, the ratio of lipid to nucleotide is between about 10,000:1 and 1000:1. Ratios in this range may be suitable when it is desired to administer small amounts of the nucleotide (e.g., in the case rare or expensive molecules). In another embodiment, the ratio is between about 8,000:1 and 4,000:1, e.g., about 6,000:1. In yet another embodiment, the ratio is between about 5,000:1 and 50:1. In yet another embodiment, the ratio of the lipid to the nucleotide is between about 20:1 and about 0.5:1. In another embodiment, the ratio of the lipid to the nucleotide is between about 1:1 and about 10:1. In yet another embodiment, the ratio of lipid to the nucleotide is about 2:1, about 3:1, or between about 1.5:1 and 3.5:1. All individual values and ranges between about 0.25:1 and about 40,000:1 are within the scope of the invention. Further values also are within the scope of the invention. The cochleate formulations also can be prepared both with and without targeting molecules (e.g., fusogenic molecules, such as Sendai virus envelope polypeptides), to target specific cells and/or tissues.

Formation of the cochleates of the invention in the above methods involves crystallization of multivalent cation with negatively charged lipids. It is evident, therefore, that all of the parameters that govern crystallization, e.g., temperature, lipid concentration, multivalent cation concentrations, rate of cation addition, pH and rate of mixing, can be utilized to regulate cochleate formation. In certain embodiments, ionic conditions can be created or adjusted to affect the efficiency of the association and/or the encochleation of the nucleotide. For example, increasing the salt concentration in a liposomal suspension can render the environment less hospitable to a hydrophobic or amphipathic nucleotide, thereby increasing liposome and cochleate loading efficiency. Ionic conditions can also affect the ultimate structure of the cochleate generated. High loads of a nucleotide can also affect the highly ordered structure observed in cochleates formed, e.g., exclusively from calcium and PS. Additionally or alternatively, pH conditions can be created or adjusted to affect the loading and structure of the resulting cochleates. Such variations can readily be manipulated by the skilled practitioner using no more than the instant specification and routine experimentation. In addition, because a cochleate is highly thermodynamically stable, once a cochleate formulation method is developed for a given product, the end product can be made predictably and reliably.

In yet another embodiment, a chelating agent (e.g., EDTA) is employed to convert cochleates to liposomes in the presence of the nucleotides and/or other cargo moiety, and then cation is added to form the cochleates.

Additionally or alternatively, nucleotides can be encochleated with high or low amounts of calcium. Accordingly, in one embodiment, a relatively low ("depressed") amount of calcium is used, e.g., between about 1 to about 10 mM. As used herein, the term "depressed amount of calcium" means a calcium concentration between about 1 and about 10 mM. In some cases, siRNA encochleated with high amounts of calcium were more active than siRNA encochleated with low amounts of calcium. Accordingly, it is believed that the use of cochleates of the invention made with higher calcium concentrations may result in more active nucleotides generally.

In one embodiment, the pH of the nucleotide is adjusted in order to induce a charge in the molecule and thereby increase its interaction with the cochleate, and in particular the phospholipid. In one embodiment, the method includes adjusting the pH of the liposomal suspension. In another embodiment, the method may include charging the base pairs of the nucleotide. For example, the pH can be adjusted to about 8.5 or about 6.0 to 6.5 or about 3.0 to 3.5 for a morpholino. Raising the pH of a liposomal suspension in the presence of morpholino causes the morpholino to associate or complex with the liposomes. Raising or lowering the pH of the nucleotide (between 3 to 11) can affect charge on the bases or backbone and enhance association with the lipid.

It has been discovered that adjusting the pH and/or charging the base pairs can improve association of the nucleotide with the cochleate. Accordingly, the method can further include the step of adjusting the pH of the nucleotide prior to or during the contact with the liposome or formation of the precipitate. Any known method of adjusting pH can be employed. For example, a nucleotide can be acidified with acidic aqueous buffer. Alternately, pH can be raised with a basic aqueous buffer. Acidic and basic buffers are known in the art, and identification of a variety of buffers would require no more than routine experimentation by one of ordinary skill in the art. Alternatively, the pH of the nucleotide can be adjusted by slow addition of an acid, e.g., hydrochloric acid, or a base, e.g., sodium hydroxide.

In yet other embodiments, the pH of the nucleotide can be adjusted prior to incorporation into the lipid precipitates. In other embodiments, the pH of the resultant a nucleotide-cochleates in solution can be adjusted using, e.g., acid or base.

The methods of the present invention can also include forming cochleates with any or all of the optional ingredients disclosed herein. For example, the cochleates can include additional cargo moieties, protonized cargo moieties, non-negative lipids, and/or aggregation inhibitors.

Any of the methods described herein can be utilized to produce anywhere from about 1 mg to about 500 g of cochleates in one batch. A smaller batch may be preferred in a laboratory setting where characterization of cochleates is desired. On the other hand, larger batches may be preferred in a manufacturing setting where mass production is desired. In some embodiments, larger batches are at least 50 g, e.g., at least 75 g.

Aggregation Inhibitors and Cochleate Size

In some embodiments, the cochleates of the present invention can optionally include one or more aggregation inhibitors. For example, in some embodiments, the cochleates of the present invention are coated with one or more aggregation inhibitors. The term "aggregation inhibitor," as used herein, refers to an agent that inhibits or reverses aggregation of cochleates. Aggregation inhibitors can be found, e.g., in WO 04/091578, the contents of which are incorporated herein it its entirety by this reference.

Such compositions are advantageous for several reasons including that smaller cochleates can allow for greater uptake by cells and rapid efficacy. Such a composition is suitable, e.g., when it is desired to rapidly and effectively deliver a nucleotide. Moreover, particle size can have a targeting affect in that some cells may take up particles of a certain size more or less effectively. Size may also affect the manner in which cochleates interact with a cell (e.g., fusion events or uptake).

The terms "coat," "coated," "coating," and the like, unless otherwise indicated, refer to an agent (e.g. an aggregation inhibitor) present at least on the outer surfaces of a cochleate. Such agents may be associated with the bilayer by incorporation of at least part of the agent into the bilayer, and/or may be otherwise associated, e.g., by ionic attraction to the cation or hydrophobic or ionic attraction to the lipid.

Suitable aggregation inhibitors that can be employed in accordance with the present invention, include but are not limited to at least one of the following: casein, κ-casein, milk, milk products (e.g., cream and half and half), albumin, serum albumin, bovine serum albumin, rabbit serum albumin, methylcellulose, ethylcellulose, propylcellulose, hydroxycellulose, hydroxymethyl cellulose, hydroxyethyl cellulose, hydroxypropyl cellulose, hydroxypropylmethyl cellulose, polyvinyl pyrrolidone, carboxymethyl cellulose, carboxyethyl cellulose, pullulan, polyvinyl alcohol, sodium alginate, polyethylene glycol, polyethylene oxide, xanthan gum, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, carrageenan, carnauba wax, shellac, latex polymers, milk protein isolate, soy protein isolate, whey protein isolate and mixtures thereof.

The amount and/or type of aggregation inhibitor and/or time of addition can be varied to modulate and/or stabilize the size and/or size distribution of a cochleate composition. Accordingly, the present invention provides a cochleate composition comprising a plurality of cochleates and an aggregation inhibitor having a desired particle size distribution.

Aggregation inhibitors can be employed to achieve cochleates that are significantly smaller and have narrower particle size distributions than compositions without aggregation inhibitors, to achieve cochleate compositions having a particle size relatively larger than that which can be achieved without or with other aggregation inhibitors, and/or to achieve a cochleate composition that has a wide particle size distribution such that the cargo moiety is released over a period of time. Moreover, in yet further embodiments, several compositions can be combined for desired release profiles, e.g., a pulsed released, or combined release.

In some embodiments, cochleate compositions of the invention have a mean diameter less than about 5, 4, 3, 2, or 1 micrometer. In other embodiments, the cochleate compositions have a mean diameter less than about 900 nm, 800 nm, 700 nm, 600 nm, 500 nm, 400 nm, 300 nm, 200 nm, or 100 nm. All individual values between these values (880, 435, 350, etc.), are meant to be included and are within the scope of this invention. In still other embodiments, cochleate compositions of the invention include cochleate populations having a mean diameter about equal to or greater than about 1 micrometer, e.g., 2, 3, 4, 5, 10, 50, or 100 micrometers. All individual values and ranges within these ranges are meant to be included and are within the scope of this invention.

In some embodiments, the size distribution is narrow relative to that observed in standard cochleates (cochleates formed without aggregation inhibitors). In some embodiments, the cochleates have a size distribution of less than about 30, 20, 10, 5, 3 or 1 μm, 900 nm, 800 nm, 700 nm, 600 nm, 500 nm, 400 nm, 300 nm, 200 nm, or 100 nm. All individual values between these values (550 nm, 420 nm, 475 nm; etc.), are meant to be included and are within the scope of this invention. Such compositions are particularly desirable where uptake by macrophages is desired. It can readily be appreciated that particle size can be adjusted to a size suitable for uptake by desired organs or cells and/or unsuitable for uptake by organs or cells. In another embodiment, a wider size distribution of cochleates is employed, e.g., about 10, 20, 50, 100, 200 . . . 500 micrometers. All individual values within these ranges are meant to be included and are within the scope of this invention. Such compositions can be useful for long term release of nucleotides.

Additionally, as discussed above, the invention contemplates combination of cochleate populations with one or more cargo moieties, one or more size distributions, and one or more mean diameter, to achieve a desired release pattern, e.g., pulsed release, delayed release and/or timed release of different cargo moieties.

Cargo Moieties

The cochleates and cochleate compositions of the present invention can further include one or more additional cargo moieties. An "additional cargo moiety" is an encochleated moiety in addition to the nucleotide of the invention, and generally does not refer to the lipid and ion employed to precipitate the cochleate. Cargo moieties include any compounds having a property of biological interest, e.g., ones that have a role in the life processes of a living organism. A cargo moiety may be organic or inorganic, a monomer or a polymer, endogenous to a host organism or not, naturally occurring or synthesized in vitro and the like.

Exemplary additional cargo moieties are disclosed in WO 04/091578, the entire contents of which are incorporated by this reference. Cargo moieties include, but are not limited to, vitamins, minerals, nutrients, micronutrients, amino acids, toxins, microbicides, microbistats, co-factors, enzymes, polypeptides, polypeptide aggregates, polynucleotides, lipids, carbohydrates, nucleotides, starches, pigments, fatty acids, monounsaturated fatty acids, polyunsaturated fatty acids, flavorings, essential oils, extracts, hormones, cytokines, viruses, organelles, steroids and other multi-ring structures, saccharides, metals, metabolic poisons, imaging agents, antigens, porphyrins, tetrapyrrolic pigments, marker compounds, medicaments, drugs and the like.

Methods of Use

In another embodiment, the invention provides methods of administering any of the compositions described herein to a host (e.g., a cell or organism). The method generally includes administering a biologically effective amount of a nucleotide-cochleate composition to a host. The cochleate compositions can include any of the compositions described herein including, e.g., compositions with additional cargo moieties and/or aggregation inhibitors.

The host can be a cell, a cell culture, an organ, a tissue, an organism, an animal etc. For example, in one embodiment, the nucleotide is delivered to a cell in the host (e.g., to a cytosol compartment of the cell).

In one embodiment the nucleotide mediates RNAi against a target mRNA in the host. In another embodiments, the nucleotide mediates translation of a target mRNA in the host. In either embodiment, although acting by a different mechanism, specific target protein synthesis preferably is reduced in the host. In some embodiments, target protein synthesis is reduced by at least about 10%, 20%, 30%, 40%, 50%, 60%, 70%, 80%, 90%, or even 100%.

Physical methods of introducing nucleotides to cells and organisms employing cochleates include contacting the cells with the cochleates or administering the cochleates to the organism by any means, e.g., orally, intramuscularly, intradermally, transdermally, intranasally, intrarectally, subcutaneously, topically, or intravenously. Nucleotide-cochleates may be introduced to or into a call using a number of mechanisms, methods, or routes, all of which are known in the art. See, e.g., WO 04/091572.

A cell or tissue with a target mRNA may be derived from or contained in any organism. The organism may be a plant, animal, protozoan, bacterium, virus, or fungus, as also described in, e.g., WO 04/091572. The cell having the target mRNA may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target mRNA and the dose of nucleotide material delivered, this process may provide partial or complete loss of function for the target mRNA in a host. A reduction or loss of mRNA expression in at least 20%, 30%, 40%, 50%, 60%, 70%, 80%, 90%, 95% or 99% or more of the host or targeted cells in the host is exemplary. Inhibition of mRNA expression refers to the absence (or observable decrease) in the level of protein and/or mRNA product from a target mRNA. Specificity refers to the ability to inhibit the target mRNA without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a micro array, antibody binding, enzyme linked immunosorbent assay (ELISA), Western blotting, radioimmunoassay (RIA), other immunoassays, and fluorescence activated cell analysis (FACS). Assays for assessing delivery and activity of the compositions of the present invention, as well as assays for mRNA expression are described, e.g., in WO 04/091572.

The nucleotide may be introduced in an amount which allows delivery of at least one copy per cell. Higher doses (e.g., at least 5, 10, 100, 500 or 1000 copies per cell) of material may yield more effective inhibition; lower doses may also be useful for specific applications.

The cochleates can be coadministered with a further agent. The second agent can be delivered in the same cochleate preparation, in a separate cochleate preparation mixed with the cochleates preparation of the invention, separately in another form (e.g., capsules or pills), or in a carrier with the cochleate preparation. The cochleates can further include one or more additional cargo moieties, such as other drugs, peptides, nucleotides (e.g., DNA and RNA), antigens, nutrients, flavors and/or proteins. Such molecules have been described in U.S. Pat. Nos. 6,153,217 (Jin et al.) and 5,994,318 (Gould-Fogerite et al.), and International Patent Publication Nos. WO 00/42989 (Zarif et al.) and WO 01/52817 (Zarif et al.). These patents are expressly incorporated by this reference.

The cochleates of the invention also can include a reporter molecule for use in in vitro diagnostic assays, which can be a fluorophore, radiolabel or imaging agent. The cochleates can include molecules that direct binding of the cochleate to a specific cellular target, or promotes selective entry into a particular cell type.

Another advantage of the present invention is the ability to modulate cochleate size. Modulation of the size of cochleates can change the manner in which the nucleotide and/or additional cargo moiety is taken up by cells. For example, in general, small cochleates are taken up quickly and efficiently into cells, whereas larger cochleates are taken up more slowly, but tend to retain efficacy for a longer period of time. Also, in some cases small cochleates are more effective than large cochleates in certain cells, while in other cells large cochleates are more effective than small cochleates.

Methods of Treatment

In another embodiment, the present invention provides for both prophylactic and therapeutic methods of treating a subject at risk of (or susceptible to) a disorder or having a disorder associated with aberrant or unwanted target gene expression or activity. The method generally includes administering to a subject a therapeutically effective amount of a nucleotide-cochleate of the invention such that the disease or disorder is treated.

The present invention provides a method for treating a subject that would benefit from administration of a composition of the present invention. Any therapeutic indication that would benefit from the cochleate compositions of the present invention can be treated by the methods of the invention. The method includes the step of administering to the subject a composition of the invention, such that the disease or disorder is treated.

Methods of treatment (prophylactic and therapeutic), including therapeutically effective amounts, are described, e.g., in WO 04/091572.

"Treatment", or "treating" as used herein, is defined as the application or administration of a therapeutic agent (e.g., antibiotics encochleated by cochleates of the invention) to a patient, or application or administration of a therapeutic agent to an isolated tissue or cell line from a patient, who has a disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease or disorder. "Treated," as used herein, refers to the disease or disorder being cured, healed, alleviated, relieved, altered, remedied, ameliorated improved or affected. For example, certain methods of treatment of the instant invention provide for administration of anti-inflammatory cochleates, such that inflammation is lessened or alleviated. Other methods of treatment of the instant invention include the administration of antifungal cochleates, such that fungal infection is relieved or remedied.

The terms "cure," "heal," "alleviate," "relieve," "alter," "remedy," "ameliorate," "improve" and "affect" are evaluated in terms of a suitable or appropriate control. A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to administration of a cargo moiety cochleate, as described herein. For example, the number of colony forming units can be determined prior to administering an echinocandin cochleate of the invention to a host. In another embodiment, a "suitable control" or "appropriate control" is a value, level, feature, characteristic, property, etc. determined in a subject, e.g., a control or normal subject exhibiting, for example, normal traits. In yet another embodiment, a "suitable control" or "appropriate control" is a predefined value, level, feature, characteristic, property, etc.

One advantage of the cochleates of the present invention is the safety and stability of the composition. Cochleates can be administered orally or by instillation without concern, as well as by the more traditional routes, such as oral, intranasal, intraoculate, intrarectal, intravaginal, intrapulmonary, topical, subcutaneous, intradermal, intramuscular, intravenous, subcutaneous, transdermal, systemic, intrathecal (into CSF), and the like. Direct application to mucosal surfaces is an attractive delivery means made possible with cochleates.

The disease or disorder treated in accordance with the present invention can be any disease or disorder that can be treated by the successful administration of the nucleotides of the invention. Exemplary diseases and disorders include neurological disorders associated with aberrant or unwanted gene expression such as schizophrenia, obsessive compulsive disorder (OCD), depression and bipolar disorder, Alzheimer's disease, Parkinson's disease, lymphoma, immune-mediated inflammatory disorders, hyperplasia, cancers, cell proliferative disorders, blood coagulation disorders, Dysfibrinogenaemia and hemophelia (A and B), dematological disorders, hyperlipidemia, hyperglycemia, hypercholesterolemia, obesity, acute and chronic leukemias and lymphomas, sarcomas, adenomas, fungal infections, bacterial infections, viral infections, a lysosomal storage disease, Fabry's disease, Gaucher's Disease, Type I Gaucher's Disease, Farber's disease, Niemann-Pick disease (types A and B), globoid cell leukodystrophy (Krabbe's disease), metachromic leukodystrophy, multiple sulfatase deficiency, sulfatidase activator (sap-B) deficiency, sap-C deficiency, $G_{M1}$-gangliosidosis, Tay-Sachs disease, Tay-Sachs B1 variant, Tay-Sachs AB variant, Acid Maltase Deficiency, Mucopolysaccharidosis, Sandhoffs disease, a cancer, an autoimmune disorder, systemic lupus erythematosis, multiple sclerosis, myasthenia gravis, autoimmune hemolytic anemia, autimmune thrombocytopenia, Grave's disease, allogenic transplant rejection, rheumatoid arthritis, ankylosing spondylitis, psoriasis, scleroderma, carcinomas, epithelial cancers, small cell lung cancer, non-small cell lung cancer, prostate cancer, breast cancer, pancreatic cancer, hepatocellular carcinoma, renal cell carcinoma, biliary cancer, colorectal cancer, ovarian cancer, uterine cancer, melanoma, cervical cancer, testicular cancer, esophageal cancer, gastric cancer, mesothelioma, glioma, glioblastoma, pituitary adenomas, inflammatory diseases, osteoarthritis, atherosclerosis, inflammatory bowel diseases (Crohns and ulcerative colitis), uveitis, eczema, chronic rhinosinusitis, asthma, a hereditary disease, cystic fibrosis, and muscular dystrophy. In some embodiments, the disease or disorder is influenza.

The method can also be used for regulating gene expression to promote greater health or quality of life, e.g., to limit cholesterol uptake or regulate lipid metabolism, weight gain, hunger, aging, or growth. Cosmetic effects such as wrinkle reduction, hair growth, pigmentation, or dermatologic disorders may also be treated.

The compositions of the present invention can be used to enhance antiviral defense, transposon silencing, gene regulation, centromeric silencing, and genomic rearrangements. The compositions of the invention can also be used to inhibit expression of other types of RNA, e.g., ribosomal RNA, transfer RNA, and small nuclear RNA.

The nucleotide cochleate compositions of the present invention can be utilized in any number of therapies involving oligonucleotides. One such treatment is for the management of opportunistic fungal infections like *Aspergillus fumigatus*, particularly in immunocompromised patients. Current treatment protocols with existing antifungal agents can still result in mortality rates of 80% in HIV patients or those undergoing cancer-related chemotherapies. However, the targeted disruption of the P-type H+-ATPase, an important plasma membrane enzyme critical to fungal cell physiology, may be an alternate and more effective way to destroy fungi such as *A. fumigatus*. This particular ATPase was cloned and selective small interfering RNA (siRNA) oligonucleotides obtained, which can knockdown the expression of this critical protein, resulting in the death of the fungus.

The essential role of the H+-ATPase in spore germination and multiplication of growing cells provides an opportunity to explore the ability of nanocochleates to efficiently deliver siRNAs targeted to the H+-ATPase of *A. fumigatus*. Given the medical importance of *A. fumigatus* and the paucity of available antifungal compounds, compositions of the present invention, e.g., siRNA cochleate compositions have the potential to be effective therapeutic alternatives.

Combination Therapies

The above methods can be employed in the absence of other treatment, or in combination with other treatments. Such treatments can be started prior to, concurrent with, or after the administration of the compositions of the instant invention. Accordingly, the methods of the invention can further include the step of administering a second treatment, such as a second treatment for the disease or disorder or to ameliorate side effects of other treatments. Such second treatment can include, e.g., any treatment directed toward reducing an immune response. Additionally or alternatively, further treatment can include administration of drugs to further treat the disease or to treat a side effect of the disease or other treatments (e.g., anti-nausea drugs).

In one embodiment, the invention provides a method for preventing in a subject, a disease or disorder which can be treated with administration of the compositions of the invention. Subjects at risk for a disease or condition which can be treated with the agents mentioned herein can be identified by, for example, any or a combination of diagnostic or prognostic assays known to those skilled in the art. Administration of a prophylactic agent can occur prior to the manifestation of symptoms characteristic of the disease or disorder, such that the disease or disorder is prevented or, alternatively, delayed in its progression.

Pharmaceutical Compositions

In some embodiments, the invention pertains to uses of the cochleates of the invention for prophylactic and therapeutic treatments as described infra. Accordingly, the cochleates of the present invention can be incorporated into pharmaceutical compositions suitable for administration. Such compositions typically comprise the cochleates of the invention and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art.

Cochleates of the present invention readily can be prepared from safe, simple, well-defined, naturally occurring substances, e.g., phosphatidylserine (PS) and calcium. Phosphatidylserine is a natural component of all biological membranes, and is most concentrated in the brain. The phospholipids used can be produced synthetically, or prepared from natural sources. Soy PS is inexpensive, available in large quantities and suitable for use in humans. Additionally, clinical studies indicate that PS is safe and may play a role in the support of mental functions in the aging brain. Unlike many cationic lipids, cochleates (which are composed of anionic lipids) are non-inflammatory and biodegradable. The tolerance in vivo of mice to multiple administrations of cochleates by various routes, including intravenous, intraperitoneal, intranasal and oral, has been evaluated. Multiple administrations of high doses of cochleate compositions to the same animal show no toxicity, and do not result in either the development of an immune response to the cochleate matrix, or any side effects relating to the cochleate vehicle.

The cochleates of the present invention can be administered to animals, including both human and non-human animals. It can be administered to animals, e.g., in animal feed or water. Methods for preparing pharmaceutical compositions containing the compositions of the present invention, including additional agents (e.g., wetting agents, emulsifiers and lubricants) used in such compositions, may be dependent upon the method of administration. Such method are known in the art, e.g., in WO 04/091572.

In some embodiments, adjuvants or immunomodulators may be added to the compositions of the present invention to stimulate an immune response. The immunomodulator can include comprise envelope proteins derived from human or animal viruses, oligonucleotides, e.g., CpG oligonucleotides, or can be chemical in nature. Specific chemical immunomodulators include, but are not limited to cytokines, chemokines and lymphokines, including, but not limited to, interferon alpha, interferon gamma, and interleukin 12. Examples of suitable animal viruses as a source of envelope protein include, but are not limited to, viruses from the following families: Arenaviridae, Bunyaviridae, Coronaviridae, Deltaviridae, Flaviviridae, Herpesviridae, Rhabdoviridae, Retroviridae, Poxyiridae, Paramyxoviridae, Orthomyxoviridae, and Togaviridae. Envelope proteins from influenza virus, Newcastle disease virus, and vaccinia virus, and Sendai virus are also encompassed in the present invention.

The pharmaceutical compositions can be included in a container, pack, or dispenser together with instructions for administration. The pharmaceutical compositions can be included in a container along with one or more additional compounds or compositions and instructions for use. For example, the invention also provides for packaged pharmaceutical products containing two agents, each of which exerts a therapeutic effect when administered to a subject in need thereof. A pharmaceutical composition may also comprise a third agent, or even more agents yet, wherein the third (and fourth, etc.) agent can be another agent against the disorder, such as a cancer treatment (e.g., an anticancer drug and/or chemotherapy) or an HIV cocktail. In some cases, the individual agents may be packaged in separate containers for sale or delivery to the consumer. The agents of the invention may be supplied in a solution with an appropriate solvent or in a solvent-free form (e.g., lyophilized). Additional components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

The present invention also includes packaged pharmaceutical products containing a first agent in combination with (e.g., intermixed with) a second agent. The invention also includes a pharmaceutical product comprising a first agent packaged with instructions for using the first agent in the presence of a second agent or instructions for use of the first agent in a method of the invention. The invention also includes a pharmaceutical product comprising a second or additional agents packaged with instructions for using the second or additional agents in the presence of a first agent or instructions for use of the second or additional agents in a method of the invention. Alternatively, the packaged pharmaceutical product may contain at least one of the agents and the product may be promoted for use with a second agent.

EXEMPLIFICATION

Example 1

Preparation of Decoy Cochleates

Formulation #1

1.5 mg H3 NF-kB Decoy in 850 µL TES buffer (pH 7.4) was combined with 3.75 mg palmitoyl L-carnitine chloride undecyl ester in 188 µL TES buffer. The resultant mixture was then passed through a 0.45 µm filter, followed by a 0.22 µm filter. 7.5 mg of DOPS in 375 µL TES buffer was then added to the mixture. The resultant mixture was again passed through a 0.45 µm filter, followed by a 0.22 µm filter. 75 µL of 0.1M calcium chloride was then added to the mixture to form aggregates of cochleates (about 1 mg/ml oligonucleotide) with a lipid:decoy ratio of about 7.5:1.

Formulation #2

1.5 mg H3 NF-kB Decoy in 300 µL TES buffer was combined with 7.5 mg palmitoyl L-carnitine chloride undecyl ester in 375 µL TES buffer. The resultant mixture was then passed through a 0.45 µm filter, followed by a 0.22 µm filter. 7.5 mg of DOPS in 375 µL TES buffer was then added to the mixture. The resultant mixture was again passed through a 0.45 µm filter, followed by a 0.22 µm filter. 7.5 mg of bovine serum albumin (BSA) in 375 µL TES buffer was then added. The resultant mixture was again passed through a 0.45 µm filter, followed by a 0.22 µm filter. 75 µL of 0.1M calcium chloride was then added to the mixture to form cochleates (about 1 mg/ml) with a lipid:decoy ratio of about 10:1. Because the decoy associated with palmitoyl L-carnitine chloride undecyl ester is not exceedingly soluble in buffer, they tend to aggregate in the middle of the cochleate, with the DOPS and calcium typically on the outside. In order to disrupt the cochleate, the solution was passed through a 26½ needle ten times. After this needle procedure, small to medium aggregates of cochleates were observed.

Formulations #3 and #4

1.5 mg H3 NF-kB Decoy in 300 µL TES buffer was combined with 15 mg palmitoyl L-carnitine chloride undecyl ester in 750 µL TES buffer. The resultant mixture was then passed through a 0.45 µm filter, followed by a 0.22 µm filter. 15 mg of DOPS in 750 µL TES buffer was then added to the mixture. The resultant mixture (Mixture A) was again passed through a 0.45 µm filter, followed by a 0.22 µm filter.

Formulation #3: To an 850 µL aliquot of Mixture A was added 70 µL of 0.1M calcium chloride to form aggregates of cochleates (about 0.77 mg/ml) with a lipid:decoy ratio of about 20:1.

Formulation #4: An 850 µL aliquot of Mixture A was treated ten times with 26½ needles in a similar manner to the cochleates of Formulation #2. 70 µL of 0.1M calcium chloride was then added to the mixture to form aggregates of cochleates (about 0.77 mg/ml) with a lipid:decoy ratio of about 20:1.

Formulations #5 and #6

3 mg PS NF-kB Decoy in 600 µL TES buffer was combined with 15 mg palmitoyl L-carnitine chloride undecyl ester in 750 µL TES buffer. The resultant mixture was then passed through a 0.45 µm filter, followed by a 0.22 µm filter. 15 mg of DOPS in 750 µL TES buffer was then added to the mixture. The resultant mixture (Mixture B) was again passed through a 0.45 µm filter, followed by a 0.22 µm filter.

Formulation #5: To a 1.0 ml aliquot of Mixture B was added 7.5 mg of bovine serum albumin (BSA) in 400 µL TES buffer. 100 µL of 0.1M calcium chloride was then added to the mixture to form cochleates (about 0.95 mg/ml) with a lipid:decoy ratio of about 10:1. These cochleates were then treated ten times with 26½ needles in a similar manner to Formulation #2 to form small aggregates of cochleates.

Formulation #6: To a 1.0 ml aliquot of Mixture B was added 400 µL TES buffer. The resultant mixture was treated ten times with 26½ needles in a similar manner to Formulation #2 followed by the addition of 100 µL of 0.1M calcium chloride to form small aggregates of cochleates (about 0.95 mg/ml) with a lipid:decoy ratio of about 10:1.

Formulation #7

1.5 mg PS NF-kB Decoy in 300 µL TES buffer (pH 7.4) was combined with 3.75 mg palmitoyl L-carnitine chloride undecyl ester in 188 µL TES buffer. The resultant mixture was then passed through a 0.45 µm filter, followed by a 0.22 µm filter. 7.5 mg of DOPS in 375 µL TES buffer was then added to the mixture. The resultant mixture was again passed through a 0.45 µm filter, followed by a 0.22 µm filter. 75 µL of 0.1M calcium chloride was then added to the mixture to form aggregates of cochleates (about 1.6 mg/ml) with a lipid:decoy ratio of about 7.5:1.

FIG. 2 shows phase contrast and fluorescence microscopic images of exemplary decoy cochleates as prepared in Formulation #3, above. Aggregates of varying sizes are composed of individual crystals of PS/Ca of less than 1 micron (shown as dark areas) encochleating the decoy (shown as lighter areas). The decoy, indicated by lighter areas in the fluorescence image, is seen as two distinct populations encased within the cochleate matrix: very small highly punctate dots, and larger, more diffuse "flowing" areas. The "Bleached Fluorescence" image allows the morphology of the "flowing Areas" to be seen more clearly.

Example 2

Analysis of Nuclear Localization

HT29 cells were plated at 50% confluence in 8 well chamber slides. 5'FAM NF-kB decoy cochleates prepared as described in Example 1 and non-cochleated decoy were then added at concentrations of 5 µM, 500 nM, 250 nM, 125 nM, 62.5 nM, 31.25 nM, and 0 to 2 wells each. The cells were then incubated for 24 h at 37° C. After 24 h, the cells were washed once with HBSS to remove excess decoy present. The cells were then fixed for 30 min by adding 2% paraformaldehyde. The nuclear stain Hoechst 33528 was then used to counterstain the cells, and coverslips were added to the slides using ProLong Antifade mounting medium for analysis. Fluorescent microscopic images analyzed utilizing Image Pro software for assessment of extent of nuclear localization of the FAM Decoy.

As shown in FIGS. 3 and 4, cochleates of both H3 and PS NFkB decoys were efficiently taken up by HT29 cells and decoy was seen in the nuclei of the cells. Formulation #2 was not analyzed for nuclear uptake, because it was expected that their large size would prevent efficient cellular uptake.

Figure 5:
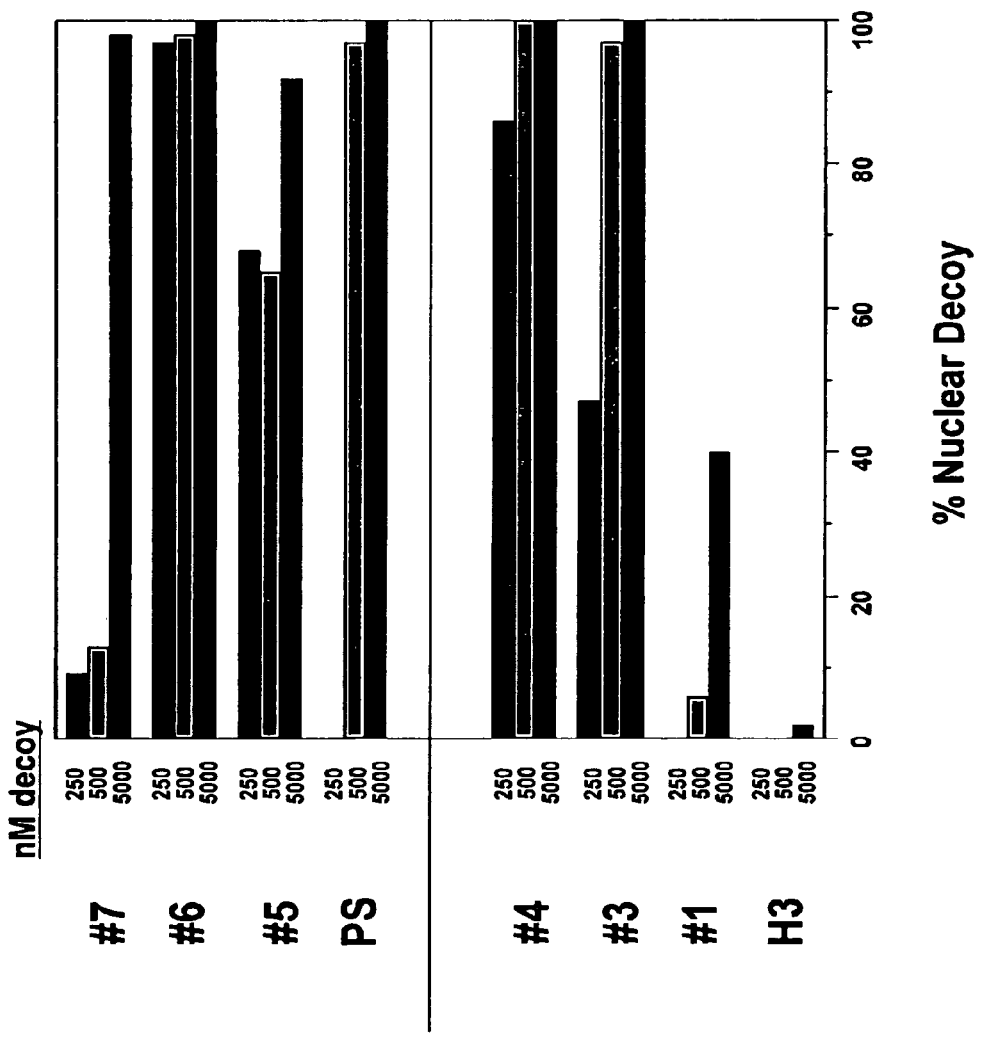
FIG. 5 is a graph showing the relative extent of nuclear localization of exemplary decoy cochleates of the present invention.

FIG. 5 is a graph showing the relative extent of nuclear localization of the FAM Decoy of each Formulation, as well as the unencochleated decoy. The background was established using cells untreated with decoy, and the results are reported as percent of cells with nuclear decoy detected. Table 1, below shows approximate increases in decoy signal for each formulation.

TABLE 1

Nuclear decoy signal

| Formulation | Morphology | Increase in Nuclear Decoy |
|---|---|---|
| H3 | | |
| #1 | Small needles | >10X |
| #3 | Medium aggregates | >20X |
| #4 | Small aggregates | >40X |
| PS | | |
| #5 | Small aggregates | >40X |
| #6 | Small aggregates | >40X |
| #7 | Small needles | 1X |

It was determined that encochleation increased uptake of H3 NF-kB Decoy. Spontaneous uptake of unencochleated H3 Decoy is generally very low. All three formulations improved the percent of transfected cells and the amount of decoy delivered to the nuclei. It was also determined that encochleation increased uptake of PS NF-kB Decoy. A large percent of cells spontaneously take up low levels of unencochleated PS Decoy at and above 500 nM. Formulations #5 and #6 dramatically improved the percent of positive cells and the amount of decoy delivered at 250 nM and encochleation generally increased the amount (brightness) of PS decoy in positive cells (not visible in figures). Finally, encochleation did not effect the ability of the decoy to localize to the nuclei.

Example 3

Encochleated Decoy Quantification

5'FAM NFkB decoy cochleates prepared as described in Example 1 and non-cochleated 5'FAM decoy were treated with EDTA, to give a final EDTA concentration of 15 mM and a pH of about 7.4-7.6. The samples were then serially diluted in PBS in UV microtiterplates. The Fluorescence measurements were taken with a Gemini EM Microplate Spectrofluorometer (Molecular Devices) at an excitation maximum of 488 nm and an emission minimum of 530 nm. The concentration of decoy in cochleates, shown below in Table 2, was quantified using a non-cochleated decoy standard curve. Fluorescence-based decoy quantification showed much lower levels of decoy in the cochleates (2-10-fold lower) when compared to the 5'FAM decoy.

TABLE 2

Concentration of decoy in cochleates

| Formulation | Est. conc. (mg/ml) | Calc. conc. (mg/ml) |
|---|---|---|
| H3 | 1.0 | 1.05 |
| #1 | 1.0 | 0.23 |
| #2 | 1.0 | 0.22 |
| #3 | 0.75 | 0.14 |
| #4 | 0.75 | 0.16 |
| PS | 1.0 | 1.08 |
| #5 | 1.0 | 0.12 |
| #6 | 1.0 | 0.21 |
| #7 | 1.3 | 0.38 |

These values were used to determine a value for the underestimation of the decoy concentration actually used in Example 2. Table 3, below, provides the results from Example 2 combined with the underestimated concentration to find a normalized increase in signal.

TABLE 3

Normalized decoy signal

| Formulation | Increase in Nuclear Decoy | Underestimation of Decoy concentration | Normalized increase in nuclear decoy signal |
|---|---|---|---|
| #1 | >10X | 4.5 | >45X |
| #3 | >20X | 7.5 | >150X |
| #4 | >40X | 6.75 | >270X |
| #5 | >40X | 9 | >360X |
| #6 | >40X | 2.1 | >200X |
| #7 | 1X | 2.8 | >3X |

Example 4

Preparation of siRNA Cochleates

Formulation #1

5 mg Flu-siRNA-U in 0.50 mL TES buffer (pH 7.4) was filtered through a 0.22 µm filter and combined with 50 mg of DOPS in 2.5 mL TES buffer to form liposomes containing the siRNA. 50 mg of palmitoyl L-carnitine chloride undecyl ester in 1.67 mL TES buffer was then added to the liposome mixture. To the resultant mixture was then added 0.408 mL of 0.1M calcium chloride to form cochleates. The mixture was then passed through a 5 µm filter, to provide small crystalline cochleates (about 1 mg/ml oligonucleotide) with a lipid:siRNA ratio of about 20:1. Such cochleates are suitable for, e.g., intravenous administration.

Formulation #2

5 mg Flu-siRNA-U in 0.50 mL TES buffer (pH 7.4) was filtered through a 0.22 µm filter and combined with 50 mg of DOPS in 2.5 mL TES buffer to form liposomes containing the siRNA. 50 mg of palmitoyl L-carnitine chloride undecyl ester in 1.67 mL TES buffer was then added to the liposome mixture. To the resultant mixture was then added 0.408 mL of 0.1M calcium chloride to form crystal cochleates (about 1 mg/ml oligonucleotide) with a lipid:siRNA ratio of about 20:1. Such cochleates are suitable for, e.g., oral administration.

Formulation #3

5 mg Flu-U-siRNA in 0.50 mL TES buffer (pH 7.4) was filtered through a 0.22 µm filter and combined with 50 mg of DOPS in 2.5 mL TES buffer to form liposomes containing the siRNA. 50 mg of palmitoyl L-carnitine chloride undecyl ester in 1.67 mL TES buffer was then added to the liposome mixture. To the resultant mixture was then added 0.408 mL of 0.1M calcium chloride to form crystal cochleates (about 1 mg/ml oligonucleotide). Cochleates were then concentrated under vacuum to provide crystal cochleates (about 4 mg/ml oligonucleotide) with a lipid:siRNA ratio of about 20:1. Such cochleates are suitable for, e.g., intranasal administration.

Formulation #4

10 mg Control-siRNA-U in 1.25 mL TES buffer (pH 7.4) was filtered through a 0.22 µm filter and combined with 100 mg of palmitoyl L-carnitine chloride undecyl ester in 10 mL TES buffer. 100 mg of DOPS in 10 mL TES buffer was then added to the mixture to form liposomes containing the siRNA. To the resultant mixture was then added 1.056 mL of 0.1M calcium chloride to form crystal cochleates (about 0.45 mg/ml oligonucleotide). Cochleates were then concentrated under vacuum to provide crystal cochleates (about 1 mg/ml oligonucleotide). The mixture was then passed through a 5 µm filter, to provide small crystalline cochleates with a lipid:siRNA ratio of about 20:1. Such cochleates are suitable for, e.g., intravenous or oral administration.

Formulation #5

5 mg Control-siRNA-U in 0.625 mL TES buffer (pH 7.4) was filtered through a 0.22 µM filter and combined with 50 mg of palmitoyl L-carnitine chloride undecyl ester in 5.0 mL TES buffer. 50 mg of DOPS in 5.0 mL TES buffer was then added to the mixture to form liposomes containing the siRNA. To the resultant mixture was then added 0.528 mL of 0.1M calcium chloride to form crystal cochleates (about 0.45 mg/ml oligonucleotide). Cochleates were then concentrated under vacuum to provide crystal cochleates (about 4 mg/ml oligonucleotide). Such cochleates are suitable for, e.g., intranasal administration.

Formulation #6

2 mg Control-siRNA-U-Cy3 in 0.2 mL TES buffer (pH 7.4) was filtered through a 0.22 µm filter and combined with 20 mg of palmitoyl L-carnitine chloride undecyl ester in 0.67 mL TES buffer. 20 mg of DOPS in 1.0 mL TES buffer was then added to the mixture to form liposomes containing the siRNA. To the resultant mixture was then added 163 µL of 0.1M calcium chloride to form crystal cochleates (about 1 mg/ml oligonucleotide) with a lipid:siRNA ratio of about 20:1. Such cochleates are suitable for, e.g., oral administration.

Formulation #7

2 mg Control-siRNA-U-Cy3 in 0.2 mL TES buffer (pH 7.4) was filtered through a 0.22 µm filter and combined with 20 mg of palmitoyl L-carnitine chloride undecyl ester in 0.67 mL TES buffer. 20 mg of DOPS in 1.0 mL TES buffer was then added to the mixture to form liposomes containing the siRNA. To the resultant mixture was then added 163 µL of 0.1M calcium chloride to form crystal cochleates (about 1 mg/ml oligonucleotide). The mixture was then passed through a 5 µm filter, to provide small crystalline cochleates with a lipid:siRNA ratio of about 20:1. Such cochleates are suitable for, e.g., intravenous administration.

Figure 6:
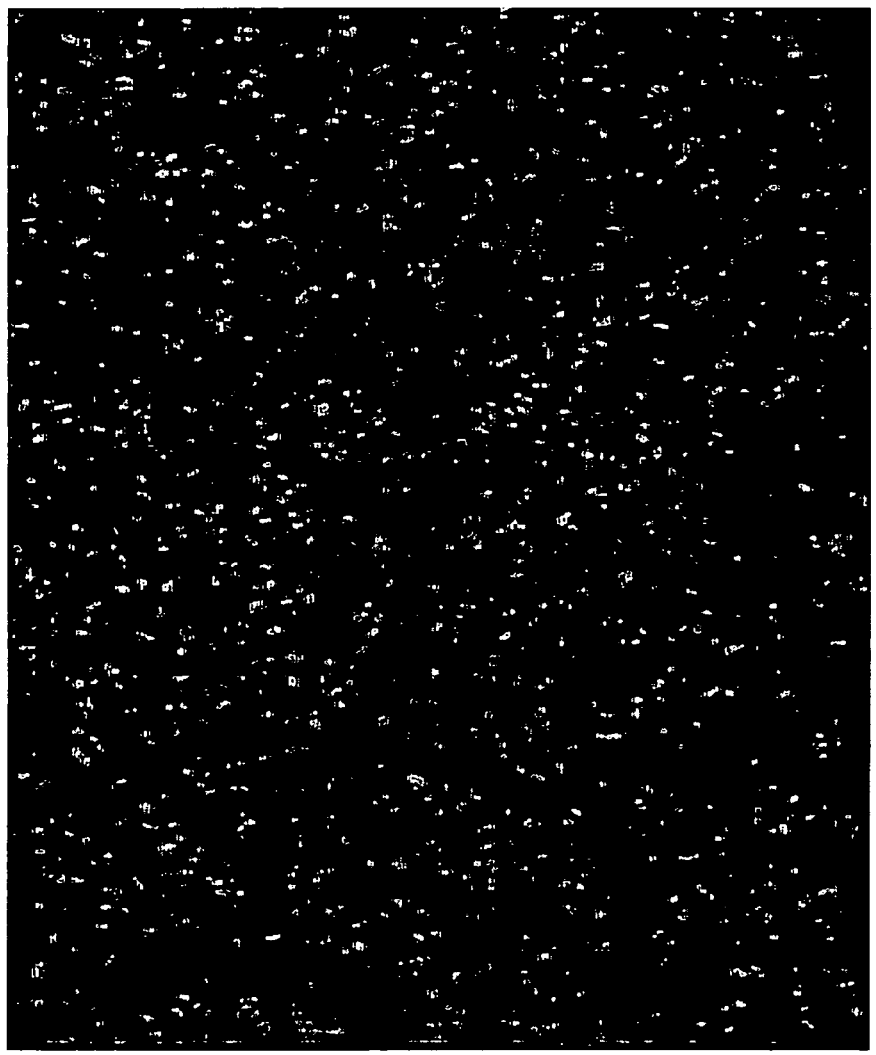
FIG. 6 depicts fluorescence microscopic images of exemplary siRNA cochleates of the present invention.

FIG. 6 shows fluorescence microscopic images of exemplary siRNA cochleates of the present invention. The siRNA are indicated by lighter areas in the fluorescence image.

Example 5

Uptake of siRNAs

3T3 cells were grown in 60 millimeter tissue culture dishes in the presence of 2 ml DMEM (Dulbecco's modified eagles medium) supplemented with 10% fetal bovine serum. A suspension of cochleates (about 10-100 µl) prepared with Cy3 tagged siRNA was added between several hours and one day after subculturing the cells. The uptake and intracellular localization of the Cy3 siRNA was observed using phase contrast and fluorescence microscopy at a magnification of 1000×.

Figure 7:
FIG. 7 shows phase contrast, fluorescence and combined microscopic images of the uptake of tagged siRNAs using exemplary cochleates of the present invention.

FIG. 7 shows phase contrast, fluorescence and combined microscopic images of the uptake of tagged siRNAs using cochleates of the present invention. The siRNA are indicated by lighter areas in the fluorescence image.

Example 6

Figure 8:
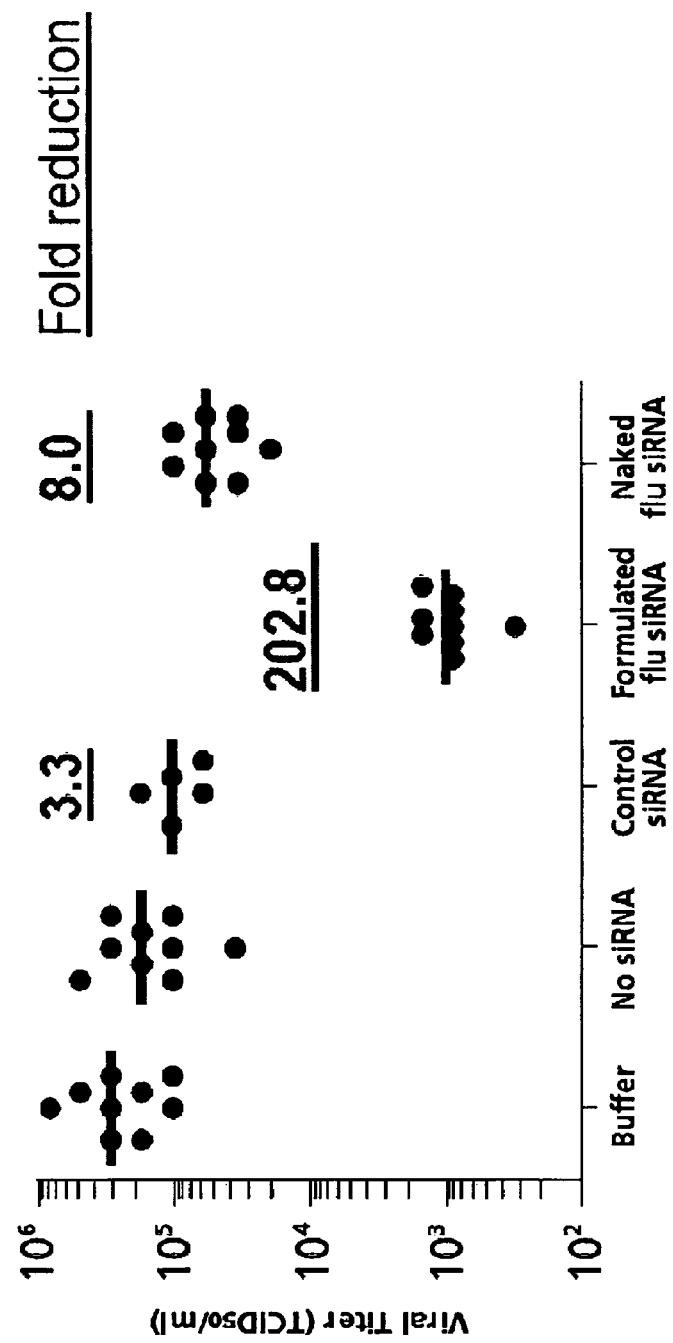
FIG. 8 shows the results of an MDCK-HA assay to measure the level of inhibition of Influenza virus production in mice after intranasal administration of exemplary cochleate formulated flu siRNA and control samples.

Intranasal Administration of Formulated siRNA Inhibits Influenza Virus Production Control and Influenza viral-specific siRNA cochleate formulations were prepared as described in Example 4. BALB/c mice were infected intranasally (100 pfu/mouse) with the PR8 serotype and then treated 2 hours later by intranasal administration to the lungs with indicated amounts of a influenza viral-specific siRNA and control siRNA in either cochleate siRNA formulation or non-formulated forms. The lungs were harvested 48 hours post-infection and viral titer was measured from lung homogenates by MDCK-HA assay as shown in FIG. 8. A 202.8-fold reduction in viral titer was observed with the cochleate siRNA formulation compared with control siRNA (3.3) and naked flu siRNA (8.0).

Example 7

Figure 9:
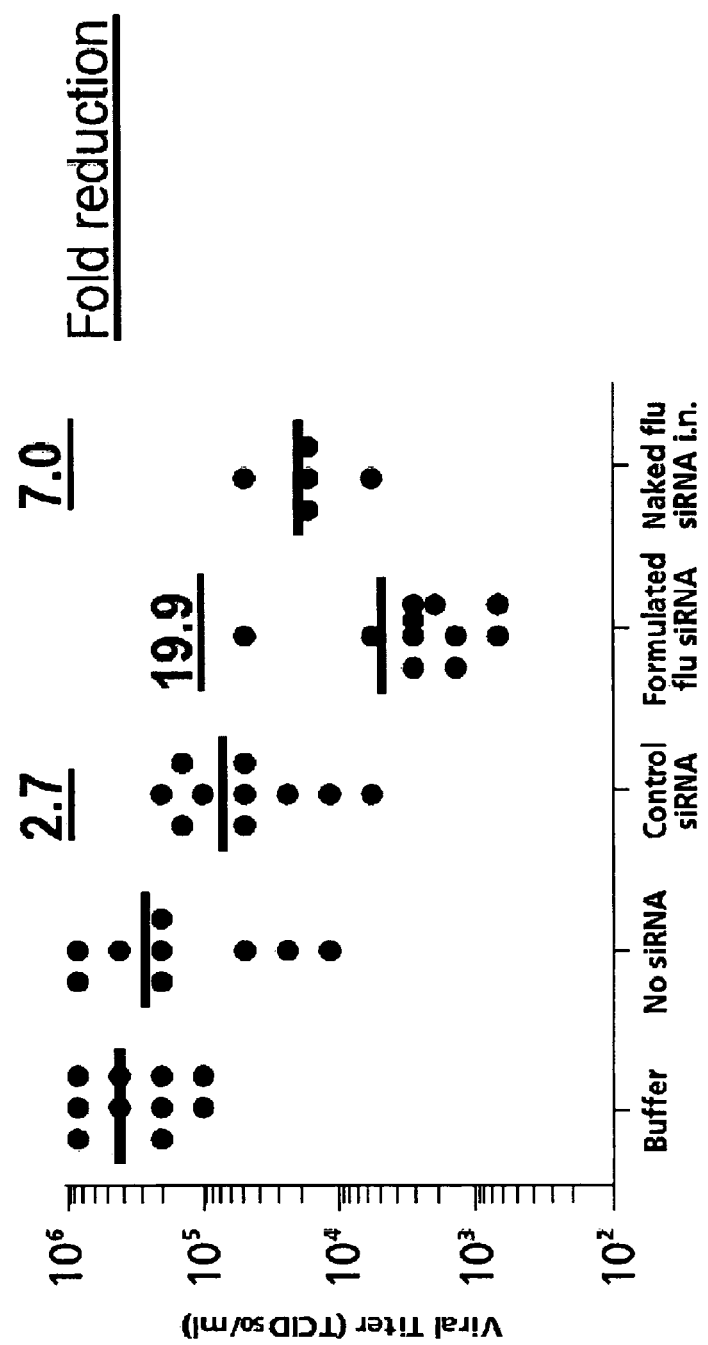
FIG. 9 shows the results of an MDCK-HA assay to measure the level of inhibition of Influenza virus production in mice after intravenous administration of exemplary cochleate formulated flu siRNA and control samples.

Intravenous Administration of Formulated siRNA Inhibits Influenza Virus Production Control and Influenza viral-specific siRNA cochleate formulations were prepared as described in Example 4. BALB/c mice were infected intranasally (100 pfu/mouse) with the PR8 serotype and then treated 2 hours later by intravenous administration (tail vein) with indicated amounts of a influenza viral-specific siRNA and control siRNA in either cochleate siRNA formulation or non-formulated forms. The lungs were harvested 48 hours post-infection and viral titer was measured from lung homogenates by MDCK-HA assay. The results of the study are shown in FIG. 9. A 19.9-fold reduction in viral titer was observed with intravenous administration of the cochleate siRNA formulation as compared with control siRNA (2.7) and naked flu siRNA (7.0).

What is claimed is:

1. A siRNA-cochleate composition comprising:

a cochleate; and a short interfering ribonucleic acid (siRNA) associated with the cochleate;

wherein the siRNA is associated with a positively charged amphiphile, wherein the positively charged amphiphile is a compound of formula (I):

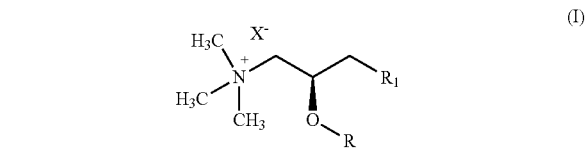

wherein:

R is selected from H, a C2-C26 acyl group and a C4-C26 aliphatic group;

$R_1$ is selected from

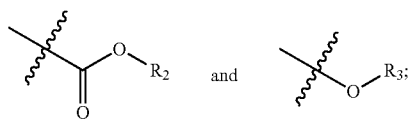

$R_2$ and $R_3$ are each independently a C4-C26 aliphatic group;

optionally one or more of R, $R_2$ and $R_3$ is:

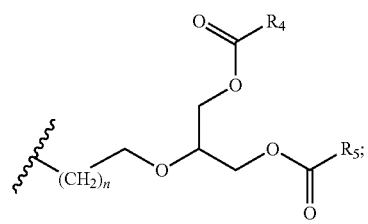

$R_4$ and $R_5$ are each independently a C3-C20 aliphatic group;

n is an integer from 1 to 3; and $X^-$ is an anion of a pharmaceutically acceptable compound.

2. The composition of claim 1, wherein R is selected from nonanoyl, dodecanoyl, myristoyl, palmitoyl, steroyl, oleoyl, oleyl, nonyl, undecyl, tetradecyl, and hexadecyl.

3. The composition of claim 1, wherein $R_1$ is

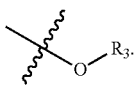

4. The composition of claim 3, wherein $R_3$ is selected from oleyl, nonyl, undecyl, tetradecyl, and hexadecyl.

5. A siRNA-cochleate composition comprising:
   a cochleate; and
   a short interfering ribonucleic acid (siRNA) associated with the cochleate;
wherein the siRNA is associated with a positively charged amphiphile, wherein the positively charged amphiphile is a compound of formula (II):

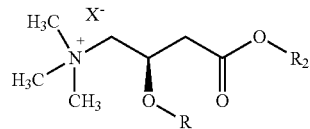

wherein:
   R is selected from H, a C2-C26 acyl group and a C4-C26 aliphatic group;
   $R_2$ is a C4-C26 aliphatic group;
   optionally one or both of R and $R_2$ is:

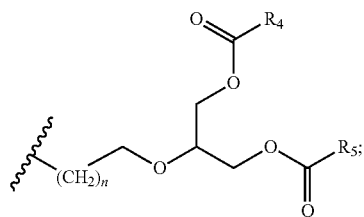

$R_4$ and $R_5$ are each independently a C3-C20 aliphatic group;
   n is an integer from 1 to 3; and
   $X^-$ is an anion of a pharmaceutically acceptable compound.

6. The composition of claim 5, wherein R is selected from nonanoyl, dodecanoyl, myristoyl, palmitoyl, steroyl, oleoyl, oleyl, nonyl, undecyl, tetradecyl, and hexadecyl.

7. The composition of claim 5, wherein $R_2$ is selected from oleyl, nonyl, undecyl, tetradecyl and hexadecyl.

8. A siRNA-cochleate composition comprising:
   a cochleate; and
   a short interfering ribonucleic acid (siRNA) associated with the cochleate;
wherein the siRNA is associated with a positively charged amphiphile, wherein the positively charged amphiphile is a compound of formula (III):

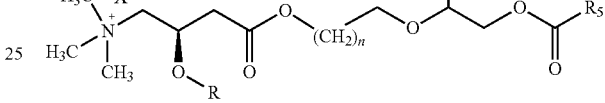

wherein:
   R is selected from a C2-C26 acyl group, a C4-C26 aliphatic group and H;
   $R_4$ and $R_5$ are each independently a C3-C20 aliphatic group;
   n is an integer from 1 to 3; and
   $X^-$ is an anion of a pharmaceutically acceptable compound.

9. The composition of claim 8, wherein R is selected from nonanoyl, dodecanoyl, myristoyl, palmitoyl, steroyl, oleoyl, oleyl, nonyl, undecyl, tetradecyl, hexadecyl, acetyl, propionyl, butyryl, valeryl, and isovaleryl.

10. The composition of claim 8, wherein —(C=O)—$R_4$ and —(C=O)—$R_5$ are each independently selected from hexanoyl, undecanoyl, myristoyl, palmitoyl and oleoyl.

* * * * *